| (12) United States Patent | (10) Patent No.: US 6,319,679 B1 |
| McKnight et al. | (45) Date of Patent: Nov. 20, 2001 |

(54) PAS KINASE

(75) Inventors: Steven L. McKnight; Kevin Gardner; Shannon Harper; Jared Rutter; Carolyn Michnoff; Carlos Amezcua, all of Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/770,170

(22) Filed: Jan. 26, 2001

(51) Int. Cl.$^7$ .......................................... C12Q 1/48
(52) U.S. Cl. ............................ 435/15; 435/194; 530/300; 530/350; 536/23.2; 536/23.5
(58) Field of Search ..................... 435/194, 15; 530/350, 530/300; 536/23.2, 23.5; 702/19

*Primary Examiner*—Nashaat T. Nashed
(74) *Attorney, Agent, or Firm*—Richard Aron Osman

(57) ABSTRACT

The invention provides methods and compositions relating to a novel kinase designated PAS Kinase (PASK). The compositions include isolated polypeptides comprising a native PASK protein or a PASK N-terminal domain and polypeptides consisting of a PASK PAS-A or PAS-B domain, as well as isolated polynucleotides encoding such polypeptides, and expression vectors and cells comprising such polynucleotides. The methods include binding assays comprising the steps of incubating a mixture comprising a subject polypeptide with a ligand under conditions wherein the polypeptide binds the ligand; and detecting binding of the polypeptide to the ligand.

13 Claims, 3 Drawing Sheets

Fig. 1A

```
         131
hPASK    NKAIFTVDAKTT..EILVANDKACGLGYSSQDLIGQKLTQFFLRSDSDVEALSEE
dmPASK   NKAIFTIDANTG..QIFIVNNKACQLLGYTSQELRNKGFFDLLNGKTESHISSLAEM
scPSK1   PQAIFTCSQEDPWQFRAANDLACLVFGISQNAIRALTLMDLIHTDSRNFV..LHKL
scPSK2   PEAIFTCSQQYPWNFKAANDLACLTFGISKNVIKALTLLDLIHTDSRNFV..LEKI hPASK    HMEAD.GHAAVFGTVVDII...SRSGEKIPVSVMKRMRQERRLCCVVLEPVERRCC
dmPASK   QIEGDEGRVVLLSGKVIEMK...TKSGGKILVSLWIRQISSDGRH..HAVAEPVER
scPSK1   LSTE..GQEMVFTGEIIGIVQPETLSSSKV..VWASFWAKRKNGLLVCVFEKVPC
scPSK2   MNAEDDNQEIVFTGETIPIVQPNSTSNNVPNLHASLWAKRKNGLLVCVFEKTPC
```

Fig. 1B

```
         341
hPASK    V F C T I S G L I T L L P D G . T I H G I N H S F A L T L F G Y G K T E L L G K N I T F L I P G F
dmPASK   V F Q N L S G L I V V D D I G . N I L M C N Q P F S L L M F G Y G Q D K I M N M H I S A I L P N F
scPSK1   S L P Y Q A G L F I V D S H T L D I V S S N K S I L K N M F G Y H F A E L V G K S I T E I I P S F
scPSK2   S L P Y Q A G L F I V D S H T L S L L S F N K S V A K N M F G L R L H E L A G S S V T K L V P S L hPASK    Y S Y M D L A Y N S S L Q L P D L A S C L D V G N E S G C G E R T L D P W Q G Q D P A E G G Q D P R I
dmPASK   G K . . D S R E E K S P N V S N . T S I T S N D W E P D T D P L V D N D S S L Q S C K K S T N R T
scPSK1   P K F L Q F I N D K Y P A L D I T L H K N K G L V L T E H F F R K I Q A E I M G D R K S F Y T S V G I
scPSK2   A D M I S Y I N K T Y P M L N I T L P E N K G L V L T E H F F R K I E A E M H H D K D S F Y T S I G L
```

Fig. 1C

```
              1005
        hPASK   LGSGAFGFV WTAVDKEKNKEVVKFIKKERVLEDCWIEDPKLGKVTLEIAILSRVE...HANIIKVLDIFENQGFFQLVMEKHGS
        dmPASK  IGRGAYGYVNMAFRNSDRLLVITKFILKEKICSQFMVKSRDCKEVPIEIHLLQTLN...HKNIVSVLDVFENDLFYQLVMEKHGS
        scPSK1  MGEGAYGKVNLCIHKKNRYIVVIKMIFKERILVDTWVRDRKLGTIPSEIQIMATLNKKPHENILRLLDFFEDDYYIETPVHGE
        scPSK2  MGEGAYGKVNLCIHNREHYIVVIKMIFKERILVDTWVRDRKLGTIPSEIQIMATLNKSQENILKLLDFFEDDYYIETPVHGE 1087
        hPASK   ..GLDLFAFIDRHPRLDEPLASYIFRQLVSAVGYLRLKDIIHRDIKDENIVIAEDFTIKLIDFGSAAYLERGKLFYTFCGTIEYC
        dmPASK  ..GMDIWTFIERRPLMDEKLGSYIFRQVADAVNYLIEQKIIHRDIKDENIIIDQNFTIKLIDFGSATFMEEGKFFSTFYGTTEYC
        scPSK1  TGCIDLFDLIEFKTNMTEFEAKLIEFKQVVAGIKHLHDQGIVHRDIKDENVIVDSKGFVKIIDFGSAAYVKSGP.FDVEVGTIDYA
        scPSK2  TCSIDLFDVIEFKKDMVEHEAKLVFKQVVASIKHLHDQGIVHRDIKDENVIVDSHGFVKLIDFGSAAYIKSGP.FDVEVGTMDYA
                                                          *              *             *

1170                                                      1251
        hPASK   APEVLMGNPYRGPELEMWSIGVTLYTLVFEENPFCELEETVEAAIHPPYL...VSKELMSIVSGLLQPVPERRTTLEKIVTDPWV
        dmPASK  SPEVLAGNRYVGPELEIEIWALGVTLYVLMFFENPFIDVEETLKAEIQIPKA..VSEQLSRLSSMLNKDPKYRCIMHQLITDPWL
        scPSK1  APEVLGGNPYEGQPQDIWAIGILLYTVVFKENPFYNIDEILEGDLKFNNAEEVSEDCIELIKSILNKCVPKRPTIDDINNDKWL
        scPSK2  APEVLGGSSYKGKPQDIWALGVILYTIIYKENPYYNIDEILEGELRFDKSEHVSEECISLIKRILTREVDKRFTIDEIYEDKWL
``` s# PAS KINASE

FIELD OF THE INVENTION

The field of this invention is protein binding assays.

BACKGROUND OF THE INVENTION

We have identified a novel enzyme designated PAS-kinase (PASK). The human version of PASK is encoded by a single gene located on chromosome 2, band q37. Analysis of genomic and cDNA clones of PASK has shown the gene to be composed of 18 coding exons covering roughly 37 kilobases of human chromosome 2. The enzyme is 1,323 amino acid residues in length and highly related in primary sequence to polypeptides specified in the genomes of flies and yeast. RT-PCR assays conducted on multiple tissues of the mouse indicate that PASK mRNA is expressed at a similar level in all tissues.

As shown in Table 1 (below), the polypeptide sequences of the human, fly and yeast versions of PASK are most conserved in three regions. Two of the three conserved regions correspond to PAS domains, designated PAS-A and PAS-B, the former being located closer to the amino terminus of the enzyme. The third conserved region of PASK encodes a serine/threonine kinase domain. When compared with all entries available in the database of protein kinases kept by Tony Hunter [1], PASK is most similar in primary amino acid sequence to the catalytic domains of the 5' AMP activated protein kinase (AMPK), its yeast ortholog SNF1, and the product of the Pim-1 oncogene.

We conducted a two-pronged approach to resolve the biological function of PASK. Biochemical experiments were carried out to study the catalytic activity of the enzyme as well as the modulatory role enacted by the two PAS domains. Complementary genetic experiments were undertaken to study the biological role of PASK in budding yeast. The latter experiments have also directed preliminary studies pertinent to the role of PASK in mammalian cells. In summary, these efforts have established PASK as a serine/threonine kinase that is regulated in cis by its two PAS domains. They have likewise implicated PASK in the regulation of translation and the balance of cell growth (cell size) and mitosis. Biophysical studies of the two PAS domains of PASK have identified PAS-A as a ligand-binding regulatory domain of the PASK enzyme. Together these studies reveal an entirely novel and unanticipated regulatory system that represents a valuable target for the development of synthetic organic compounds capable of regulating the mitotic growth of mammalian cells.

Limited aspects of this disclosure were presented at the 19th International Conference on Magnetic Resonance in Biological Systems at Florence, Italy in August 2000; see, *Structural studies of PAS domains: Insight into the link between ligand and protein binding*, K H Gardner, C A Amezcua and S M Harper, Aug. 25, 2000, 19th Intrnl Conf Magnetic Resonance in Biological Systems, Florence, Italy; and *Solution structure and dynamics of a eukaryotic PAS domain: Evidence for a flexible ligand binding region*, C A Amezcua, S M Harper and K H Gardner, Aug. 21, 2000, 19th Intrnl Conf Magnetic Resonance in Biological Systems, Florence, Italy. Genbank accession KIAA0135 has sequence similarity to the disclosed human PASK.

SUMMARY OF THE INVENTION

The invention provides methods and compositions relating to a novel kinase designated PAS Kinase (PASK). The compositions include isolated polypeptides comprising a PASK N-terminal domain, particularly a native PASK protein, and polypeptides consisting of, or consisting essentially of, a PASK PAS-A or PAS-B domain, as well as isolated polynucleotides encoding such polypeptides, and expression vectors and cells comprising such polynucleotides.

The subject methods include binding assays comprising the steps of incubating a mixture comprising a subject polypeptide with a ligand under conditions wherein the polypeptide binds the ligand; and detecting the binding of the polypeptide to the ligand. In particular embodiments, the assay is a kinase assay wherein the ligand is a substrate, the mixture further comprises a nucleoside triphosphate, the binding effects phosphorylation of the substrate, and the detecting step comprises detecting the phosphorylated substrate. In other embodiments, the assay is a NMR-based assay wherein the detecting step comprises detecting an NMR shift in the mixture.

BRIEF DESCRIPTION OF THE FIGURES

FIG. 1A shows an alignment of the PASK PAS-A domains of human (amino acids 131–237 of SEQ ID NO:2), fly (amino acids 72–177 of SEQ ID NO:4) and yeast (amino acids 460–564 of SEQ ID NO:6 and amino acids 288–397 of SEQ ID NO:8).

FIG. 1B shows an alignment of the PASK PAS-B domains of human (amino acids 341–439 of SEQ ID NO:2), fly (amino acids 280–375 of SEQ ID NO:4) and yeast (amino acids 744–843 of SEQ ID NO:6 and amino acids 522–621 of SEQ ID NO:8).

FIG. 1C shows an alignment of the PASK kinase domains of human (amino acids 1005–1251 of SEQ ID NO:2), fly (amino acids 582–828 of SEQ ID NO:4) and yeast (amino acids 1102–1354 of SEQ ID NO:6 and amino acids 847–1099 of SEQ ID NO:8). The three phosphorylatable activation loop residues are marked with a star.

DESCRIPTION OF PARTICULAR EMBODIMENTS OF THE INVENTION

The nucleotide sequences of cDNAs encoding native PASK polypeptides from human, D. Melanogaster, and yeast (two variants) are shown as SEQ ID NOS:1, 3, 5 and 7, respectively, and the full translates are shown as SEQ ID NOS:2, 4, 6 and 8, respectively. As described in further detail below, these translates comprise an N-terminal functionality, PAS-A and PAS-B domains and a kinase domain.

The subject polypeptides are isolated or pure: an "isolated" polypeptide is unaccompanied by at least some of the material with which it is associated in its natural state, preferably constituting at least about 0.5%, and more preferably at least about 5%, more preferably at least about 50% by weight of the total polypeptide in a given sample and a pure polypeptide constitutes at least about 90%, and preferably at least about 99% by weight of the total polypeptide in a given sample. The polypeptides and polypeptide domains may be synthesized, produced by recombinant technology, or purified from mammalian, preferably human cells. They may be joined, covalently or noncovalently, with a wide variety of conjugates, including labels, tags, etc., particularly other polypeptide sequences. A wide variety of molecular and biochemical methods are available for biochemical synthesis, molecular expression and purification of the subject compositions, see e.g. Molecular Cloning, A Laboratory Manual (Sambrook, et al. Cold Spring Harbor Laboratory), Current Protocols in Molecular Biology (Eds. Ausubel, et al., Greene Publ. Assoc., Wiley-Interscience, NY) or that are otherwise known in the art.

PASK N-terminal domain polypeptides, including the human PASK N-terminal domain (residues 1–89 of SEQ ID NO:2)and functional fragments thereof, elicit PASK specific antibody in a heterologous host (e.g. a rodent or rabbit), etc. Accordingly, these polypeptides provide PASK-specific antigens and/or immunogens, especially when coupled to carrier proteins (see, e.g. Harlow and Lane (1988) Antibodies, A Laboratory Manual, Cold Spring Harbor Laboratory). For example, polypepetides corresponding to PASK-specific N-terminal domain subsequences are covalently coupled to keyhole limpet antigen (KLH) and the conjugate is emulsified in Freunds complete adjuvant. Laboratory rabbits are immunized according to conventional protocol and bled. The presence of PASK-specific antibodies is assayed by solid phase immunosorbant assays using immobilezed PASK polypepetides of SEQ ID NO:2, see, e.g. Table 1.

Table 1. Immunogenic N-terminal PASK polypepetides eliciting PASK-specific rabbit polyclonal antibody: PASK polypeptide-KLH conjugates immunized per protocol described above.

| PASK Polypeptide Sequence | Immunogenicity |
| --- | --- |
| SEQ ID NO: 2, residues 1–10 | +++ |
| SEQ ID NO: 2, residues 12–21 | +++ |
| SEQ ID NO: 2, residues 20–29 | +++ |
| SEQ ID NO: 2, residues 32–49 | +++ |
| SEQ ID NO: 2, residues 52–61 | +++ |
| SEQ ID NO: 2, residues 65–79 | +++ |
| SEQ ID NO: 2, residues 77–89 | +++ |

The amino acid sequences of the subject polypeptides are used to back-translate polypeptide-encoding nucleic acids optimized for selected expression systems (Holler et al. (1993) Gene 136, 323–328; Martin et al. (1995) Gene 154, 150–166) or used to generate degenerate oligonucleotide primers and probes for use in the isolation of natural PASK polypeptide-encoding nucleic acid sequences ("GCG" software, Genetics Computer Group, Inc, Madison Wis.). PASK polypeptide-encoding nucleic acids are used in expression vectors and incorporated into recombinant host cells, e.g. for expression and screening, transgenic animals, e.g. for functional studies such as the efficacy of candidate drugs for disease associated with PASK-modulated cell function, etc.

The invention also provides nucleic acid hybridization probes and replication/amplification primers having a PASK N-terminal domain encoding cDNA sequence or fragments thereof sufficient to effect specific hybridization thereto (i.e. specifically hybridize with the corresponding PASK N-terminal domain cDNA). Such primers or probes are at least 12, preferably at least 24, more preferably at least 36 and most preferably at least 96 bases in length. Demonstrating specific hybridization generally requires stringent conditions, for example, hybridizing in a buffer comprising 30% formamide in 5×SSPE (0.18 M NaCl, 0.01 M NaPO$_4$, pH7.7, 0.001 M EDTA) buffer at a temperature of 42° C. and remaining bound when subject to washing at 42° C. with 0.2×SSPE; preferably hybridizing in a buffer comprising 50% formamide in 5×SSPE buffer at a temperature of 42° C. and remaining bound when subject to washing at 42° C. with 0.2×SSPE buffer at 42° C. PASK nucleic acids can also be distinguished using alignment algorithms, such as BLASTX (Altschul et al. (1990) Basic Local Alignment Search Tool, J Mol Biol 215, 403–410).

Table 2. Exemplary PASK nucleic acids which hybridize with a strand of SEQ ID NO:1 under Conditions I and/or II.

| PASK Nucleic Acids | Hybridization |
| --- | --- |
| SEQ ID NO: 1, nucleotides 1–24 | + |
| SEQ ID NO: 1, nucleotides 25–48 | + |
| SEQ ID NO: 1, nucleotides 49–72 | + |
| SEQ ID NO: 1, nucleotides 73–96 | + |
| SEQ ID NO: 1, nucleotides 97–120 | + |
| SEQ ID NO: 1, nucleotides 121–144 | + |
| SEQ ID NO: 1, nucleotides 145–168 | + |
| SEQ ID NO: 1, nucleotides 169–192 | + |
| SEQ ID NO: 1, nucleotides 193–216 | + |
| SEQ ID NO: 1, nucleotides 217–240 | + |
| SEQ ID NO: 1, nucleotides 242–265 | + |
| SEQ ID NO: 1, nucleotides 391–711 | + |
| SEQ ID NO: 1, nucleotides 1021–1317 | + |

The subject nucleic acids are of synthetic/non-natural sequences and/or are isolated, i.e. unaccompanied by at least some of the material with which it is associated in its natural state, preferably constituting at least about 0.5%, preferably at least about 5% by weight of total nucleic acid present in a given fraction, and usually recombinant, meaning they comprise a non-natural sequence or a natural sequence joined to nucleotide(s) other than that which it is joined to on a natural chromosome. Recombinant nucleic acids comprising native PASK cDNAs, or fragments thereof, contain such sequence or fragment at a terminus, immediately flanked by (i.e. contiguous with) a non-native sequence (a sequence other than that which it is joined to on a natural chromosome), or immediately flanked by a native flanking region of fewer than 2000, preferably fewer than 500, more preferably fewer than 100 nucleotides. While the nucleic acids are usually RNA or DNA, it is often advantageous to use nucleic acids comprising other bases or nucleotide analogs to provide modified stability, etc.

The subject nucleic acids find a wide variety of applications including use as translatable transcripts, hybridization probes, PCR primers, diagnostic nucleic acids, etc.; use in detecting the presence of PASK genes and gene transcripts and in detecting or amplifying nucleic acids encoding additional PASK homologs and structural analogs. In diagnosis, PASK hybridization probes find use in identifying wild-type and mutant PASK alleles in clinical and laboratory samples. Mutant alleles are used to generate allele-specific oligonucleotide (ASO) probes for high-throughput clinical diagnoses. In therapy, therapeutic PASK nucleic acids are used to modulate cellular expression or intracellular concentration or availability of active PASK.

The invention provides efficient methods of identifying agents, compounds or lead compounds for agents active at the level of a PASK modulatable cellular function. Generally, these screening methods involve assaying for compounds which modulate the interaction of a subject PASK polypeptide with a ligand and/or natural binding target. A wide variety of assays for binding agents are provided including labeled in vitro protein-protein binding assays, immunoassays, cell based assays, etc. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development.

In vitro binding assays employ a mixture of components including a PASK polypeptide, which may be part of a fusion product with another peptide or polypeptide, e.g. a tag for detection or anchoring, etc. The assay mixtures comprise a ligand, which term is used generically to encompass specific binding targets including substrates, preferably small molecule ligands as opposed to large molecule ligands such as protein ligands. In a particular embodiment, the binding target is a substrate of PASK kinase activity. The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like ATP or ATP analogs (for kinase assays), salts, buffers, neutral proteins, e.g. albumin, detergents, protease inhibitors, nuclease inhibitors, antimicrobial agents, etc. may be used.

The resultant mixture is incubated under conditions whereby, but for the presence of the candidate pharmacological agent, the PASK polypeptide specifically binds the ligand with a reference binding affinity. The mixture components can be added in any order that provides for the requisite bindings and incubations may be performed at any temperature which facilitates optimal binding. Incubation periods are likewise selected for optimal binding but also minimized to facilitate rapid, high-throughput screening.

After incubation, the agent-biased binding between the PASK polypeptide and one or more ligands is detected by any convenient way. For PASK kinase assays, 'binding' is generally detected by a change in the phosphorylation of a substrate. In this embodiment, kinase activity may be quantified by the transfer to the substrate of a labeled phosphate, where the label may provide for direct detection as radioactivity, luminescence, optical or electron density, etc. or indirect detection such as an epitope tag, etc. A variety of methods may be used to detect the label depending on the nature of the label and other assay components, e.g. through optical or electron density, radiative emissions, nonradiative energy transfers, etc. or indirectly detected with antibody conjugates, etc.

A difference in the binding affinity of the PASK polypeptide to the ligand in the absence of the agent as compared with the binding affinity in the presence of the agent indicates that the agent modulates the binding of the polypeptide to the ligand. A difference, as used herein, is statistically significant and preferably represents at least a 50%, more preferably at least a 90% difference.

The following experimental section and examples are offered by way of illustration and not by way of limitation.

EXAMPLES

Biochemical properties of the PASK enzyme. A recombinant baculovirus was engineered to overexpress human PASK enzyme in cultured insect cells. The enzyme was expressed as a fusion with a His$_6$ tag at its amino terminus such that the recombinant polypeptide could be purified by Ni-affinity chromatography. Routine enzyme preparations were harvested from 0.8 liter of cultured Sf-9 cells. Cells were lysed by dounce homogenization in 50 mM Tris-HCl, pH 8.0, 100 mM NaCl, 0.04% β-mercaptoethanol ("lysis buffer") and spun at 100,000×G for one hour to remove insoluble debris. Soluble material (~50 ml) was then applied to a 3 ml bed volume of Ni-affinity resin. Following application and 50× column volume wash, bound material was eluted with storage buffer (50 mM HEPES, pH 7.4, 100 mM NaCl, 1 mM DTT, 1 mM EDTA) supplemented with 250 mM imidazole. Eluted material was sequentially subjected to Mono-Q, anion-exchange chromatography, and eluted with increasing NaCl concentration. Fractions were evaluated by SDS-PAGE to identify PASK enriched fractions, pooled and dialyzed against storage buffer supplemented with 10% glycerol. Typical enzyme preparations yield 0.5 mg of intact PASK enzyme judged to be greater than 95% pure by visual inspection of Coomassie-stained SDS-PAGE gels.

Purified PASK was observed to become phosphorylated when exposed at room temperature to ATP and magnesium. Protein dilution studies revealed that the level of PASK phosphorylation diminished significantly upon dilution, indicating that phosphorylation occurs in trans. As will be shown subsequently, phosphorylation significantly elevates the activity of PASK by enhancing its $K_m$ for substrate without altering the catalytic rate constant of the enzyme. Mass spectrometry was employed to identify the sites of auto-phosphorylation suffered by PASK in response to ATP. The major sites of phosphorylation are restricted to two short sequences, one corresponding to the putative activation loop of the, catalytic domain and another corresponding to a serine-rich segment of the polypeptide located on the immediate carboxyl terminal side of the catalytic domain. Roughly 2 moles of phosphate were observed to modify a tryptic peptide encompassing the putative activation loop of PASK, and an additional 3–4 moles of phosphate were observed to modify the C-terminal, serine-rich segment of the enzyme.

Kinetic data were used to characterize the activities of PASK enzyme samples derived without modification from baculovirus and following pre-phosphorylation in the presence of ATP. Enzyme activity was monitored using a synthetic substrate bearing the sequence $NH_2$-AMARAASAAALARRR-$CO_2H$ (AMARA peptide, SEQ ID NO:9). The serine residue in this peptide is known to be phosphorylated by both AMPK and Snf1 [2], both of which are exceedingly similar in primary amino acid sequence to the catalytic domain of PASK. The three arginine residues located at the carboxyl terminus of the AMARA peptide allow avid binding to phosphocellulose paper, thereby facilitating quantitation of $^{32}P$ incorporation catalyzed by PASK from [γ-$^{32}P$]ATP. Whereas the observed $V_{max}$ for the two enzyme samples was equivalent, $K_m$ for substrate differed significantly. The prephosphorylated enzyme was observed to have a 6.5-fold lower $K_m$ for substrate than the unmodified enzyme (Table 3). Moreover, lambda phosphatase treatment generated an enzyme which had 7-fold lower activity than the unmodified enzyme, and this treatment was fully reversible by allowing the enzyme to autophosphorylate in the presence of ATP.

Having mapped sites of phosphorylation to two segments of PASK, mutated derivatives of the enzyme were produced as a means of assessing the effects of phosphorylation on enzyme activity. The putative activation loop of PASK can be identified according to extensive studies on AMPK, one of the two closest relatives of PASK. It is known that threonine residue 172, located within the activation loop of AMPK, must be phosphorylated in order to support significant catalytic activity [3]. Mutated derivatives of PASK were generated wherein serine residue 1149, threonine residue 1161 (which aligns exactly with T172 of AMPK), and threonine residue 1165 were individually changed to alanine. All three of these residues map to a tryptic peptide that is autophosphorylated by PASK. As shown in Table 3, the S to A mutation at residue 1149 (S1149A) did not significantly alter either the catalytic rate or $K_m$ for substrate. The T to A mutation at residue 1165 (T1165A) completely eliminated all detectable activity. Finally, the T to A mutation at residue 1161 (T1161A) led to the formation of an enzyme that was insufficiently stable to be purified from baculovirus and tested for enzymatic activity. Given the observation that two moles of phosphate were detected by mass spectrometric analysis of the tryptic peptide covering the activation loop of PASK, we tentatively conclude that the fully active enzyme is phosphorylated on threonine residues 1161 and 1165. These data indicate that PASK can, in trans, phosphorylate itself in a manner that mobilizes the activation loop of the enzyme and substantially enhances the avidity of the enzyme for substrate.

truncated polypeptide. Although $K_m$ for substrate was unaffected, this truncated variant exhibited a catalytic rate constant ($V_{max}$) 18-fold higher than the native enzyme (Table 3). In addition to this apparently derepressed basal activity, the truncated enzyme is not subject to regulation by phosphorylation. In contrast to the native enzyme, the lambda phosphatase-treated enzyme and the enzyme pre-incubated with magnesium and ATP showed identical catalytic activity to the unmodified protein. In summary we conclude that the catalytic activity of PASK is negatively regulated by amino terminal segments of the enzyme, particularly corresponding to the two PAS domains of the enzyme. Likewise the $K_m$ for substrate of this enzyme can be modified by phosphorylation of two threonine residues corresponding to the activation loop of the kinase domain.

In summary, biochemical studies of PASK have described an enzyme that is fundamentally very similar to the AMPK and Snf1 enzymes. Like PASK, AMPK activity is repressed

TABLE 3

Kinetic constants, $K_m$ and $V_{max}$, for wildtype and mutant forms of PASK using peptide substrate.

| | Pre-phosphorylated | | | | Untreated | | | |
|---|---|---|---|---|---|---|---|---|
| Enzyme | $K_m$(mM) | SE | $V_{max}$ | SE | $K_m$(mM) | SE | $V_{max}$ | SE |
| wildtype | 0.2 | 0.05 | 0.2 | NS | 1.3 | 0.3 | 0.1 | NS |
| S1149A | 0.6 | 0.05 | 0.1 | NS | | | | |
| T1161A | | N/A | | | | | | |
| T1165A | Catalytically inactive | | | | | | | |
| S1273, 77, 80A | 0.3 | NS | 0.4 | NS | | | | |
| S1287, 89A | 0.2 | NS | 0.1 | NS | | | | |
| S1273–1289A | 0.2 | NS | 0.1 | NS | | | | |
| PASK ΔN | 0.3 | NS | 2.8 | NS | | | | |

For this data table, enzyme assays were performed as described herein. PASK concentrations (0.5–2 μg/ml) were determined to have linear rates with respect to protein concentration and time. Kinetic constants were determined using peptide substrate concentrations between 0.06–1 mM. The data were fit to a non-linear Michaelis-Menten equation using the GraphPad Prism 2.0 program. $V_{max}$ values given are μmol/min/mg. NS indicates an SE less than 0.05.

Three additional variants of the enzyme were engineered, expressed and studied in functional assays to assess the potential relevance of phosphorylation in the serine-rich, carboxyl-terminal domain of PASK. One mutant changed serine residues 1273, 1277 and 1280 to alanine (S1273,77, 80), a second mutant changed serine residues 1287 and 1289 to alanine (S1287,89A), and a third mutant simultaneously changed all five serines to alanine (S 1273–89A). Each of the three mutated enzymes were expressed in baculovirus, purified and tested for both substrate avidity and catalytic rate. All three variants exhibited activities similar to the native enzyme.

A final series of experiments was conducted to investigate the influence of the amino terminal segment of PASK on catalytic activity of the enzyme. The only sequence conservation identifiable among the amino terminal segments of human, fly and yeast enzymes are two PAS domains (FIGS. 1A–1C). A truncated variant lacking both PAS domains (PASK ΔN) was engineered and expressed in baculovirus-infected Sf-9 cells. This variant of the human enzyme removed 948 residues on the amino-terminal side of the catalytic, serine/threonine kinase domain, and was expressed with a $His_6$ tag at the amino terminus of the by the non-catalytic regulatory domain of the enzyme (reviewed in [4]). When the regulatory domain is derepressed by increased AMP concentration, or is removed by engineered deletion, the catalytic rate of the kinase domain is substantially enhanced [5, 6]. The amino acid sequence of the catalytic domain of PASK is more similar to those of the AMPK/Snf1 and Pim1 enzymes than any other proteins in public databases, and like the AMPK/Snf1 and Pim1 enzymes, this catalytic domain is subject to phosphorylation-mediated activation in its activity for substrate. Moreover, the amino terminal domain of PASK, which contains two PAS domains, negatively regulates the catalytic activity of its serine/threonine kinase domain in cis—as does the regulatory domain of AMPK/Snf1. Finally, the PAS domains of PASK can perform a sensing function.

Genetic studies of PASK in budding yeast. The genome of the budding yeast, *Saccharomyces cerevesiae*, contains genes encoding two highly related forms of the PASK enzyme. One gene, designated PSK1, is located on the left arm of chromosome 1, corresponding to the open reading frame (ORF) YAL017W. The other, designated PSK2, is located on the left arm of chromosome 15, corresponding to ORF YOL045W. The two forms of yeast PASK are more related in primary amino acid sequence to one another than either are to the enzymes encoded by flies or humans. As such, we tentatively conclude that they arose as a duplication subsequent to the evolutionary divergence between yeast and the other metazoan organisms presently under study. The data indicate, however, that the yeast forms of PASK represent bona fide orthologs of the metazoan enzymes. The amino acid sequence of the catalytic domains of the two yeast enzymes are more highly related to those of the metazoan PASK enzymes than any other protein kinase, including all protein kinases encoded by the genome of *S. cerevesiae*. The same holds for both PAS domains of the two yeast enzymes. The PAS-A domains of both yeast enzymes are more highly related in primary amino acid sequence to the PAS-A domains of metazoan PASK enzymes than any PAS domain available in public databases. Likewise, the PAS-B domains of the yeast enzymes are more highly related to the PAS-B domains of metazoan PASKs than any other PAS domain. Finally, we have obtained unequivocal evidence that human PASK effectively complements the growth defects of yeast strains lacking both PSK1 and PSK2 enzymes (see below).

The individual yeast PSK1 and PSK2 genes were deleted by homologous recombination. In both cases a targeting vector was prepared to replace the entire open reading frame with a selectable marker. Evidence of successful deletion of each gene was confirmed by Southern blotting, yet no obvious phenotypic effect on growth under normal conditions was observed. A doubly-deleted strain (psk1 psk2) was generated by eliminating the PSK2 gene from a haploid, psk1 mutant strain. Again, no obvious effects on vegetative growth were observed. The doubly-deleted strain was then subjected to a wide range of culture conditions in an effort to identify conditions that might reveal differences between wildtype yeast, singly-mutated variants and the doubly-deficient strain. Among 50 prototypical growth conditions tested [7], two were observed to differentially affect the growth of the strain lacking both PSK1 and PSK2 genes. Cultures containing elevated levels of zinc (10 mM), when incubated at 38° C., supported the growth of wildtype yeast to a more substantive degree than the psk1 psk2 double mutant. Under such conditions the PSK2-deleted strain grew at an intermediate level, whereas the PSK1-deficient strain was similar to wildtype. Very similar observations were made when vegetative growth at 38° C. was monitored on minimal-media culture plates with galactose rather than glucose as the carbon source. Under such conditions, the wildtype strain grew well, psk1 cells grew at a slightly reduced rate, psk2 cells grew at a markedly reduced rate, and the psk1 psk2 double mutant grew very poorly. Under both conditions, reintroduction of PSK2 on a plasmid completely restored growth to wildtype levels.

Having established culture conditions capable of distinguishing vegetative growth rate, efforts were made to identify high-copy suppressors of the psk1 psk2 double mutant phenotype. Two independently generated libraries of yeast genomic DNA, carried on a high-copy plasmid bearing the yeast URA3 gene (pRS426) [8], were transformed into the double mutant. Cells were initially selected on minimal media culture plates supplemented with glucose, yet lacking uracil. Three to four days later Ura$^+$ colonies were scraped from each dish, pooled and plated onto minimal media culture plates with galactose and incubated at 38° C. Under such conditions, cells of the psk1 psk2 double mutant fail to grow. When transformed with either of the two genomic libraries, however, evidence of high-copy suppression was observed in the form of healthy colonies. Suppressing plasmids were rescued from individual colonies, transformed into *E. coli*, isolated and sequenced in order to identify putative high-copy suppressors. This effort led to the isolation and identification of roughly 50 high-copy suppressors of the psk1 psk2 double mutant phenotype. Among these, we focused our attention on clones that were retrieved a minimum of two independent times, amounting to fifteen independent genes (Table 4). Each of these genes was retransformed into psk1 psk2 mutants and the suppressing phenotype was confirmed. Two of the suppressing genes are the PSK genes themselves, demonstrating the validity of the screen. Three of the genes encode proteins involved in sugar metabolism; including phosphoglucose mutase 1 (Pgm1p), phosphoglucose mutase 2 (Pgm2p), and Snf1 interacting protein (Sip1p). Pgm1p and Pgm2p are functionally redundant and represent critical enzymes in the conversion of galactose to glucose [9, 10], and Sip1p is a positive regulator of the Snf1p kinase controlling alternate carbon source utilization [11 ]. A fifth gene repeatedly isolated in the suppressor screen, designated DDP1, encodes diadenosine polyphosphate hydrolase [12, 13].

Among the remaining ten genes that were retrieved at least two independent times in the high-copy suppressor screen, seven—and possibly two others—encode products involved in RNA metabolism or translation. These include: (i) the DED1 and DBP1 genes—both of which encode RNA helicases involved in translation initiation [14–16]; (ii) EDC1—which encodes an enhancer of mRNA decapping [17] (iii) RPR1 and POP4—which respectively encode the RNA and a protein component of RNaseP [18, 19]; (iv) tG(CCC)D which encodes a glycine tRNA [20]; and (v) RDN which encodes the RNA subunits of the ribosome [21]. Additionally, plasmids containing the YDL189W ORF were recovered multiple, independent times in the high-copy suppressor screen. Although no function has been ascribed to this gene, the encoded protein contains an R3H single-stranded nucleic acid binding domain [22], indicating that this gene product may also be involved in RNA metabolism or translation. Finally, the CPA1 gene encoding carbamoyl phosphate synthetase also emerged as a bona fide high-copy suppressor of the psk1 psk2 double mutant phenotype. Although the product of this gene acts at the first catalytic step of arginine biosynthesis [23], Cpa1p translation is tightly regulated via a $\mu$-ORF in its 5'UTR [24, 25].

TABLE 4

High-copy suppressors of psk1 psk2 mutation.

| Gene | # | Description |
| --- | --- | --- |
| PSK1/PSK2 | 4 | PAS Kinase |
| PGM1/PGM2 | 3 | Galactose Metabolism |
| SIP1 | 5 | Glucose Repression |
| DDP1 | 4 | Diadenosine Polyphosphate Hydrolase |
| DED1 | 3 | RNA Helicase |
| DBP1 | 2 | RNA Helicase |
| EDC1 | 2 | Enhancer OF mRNA Decapping |
| RPR1 | 2 | RNase P RNA Subunit |
| POP4 | 3 | RNase P/RNase MRP Subunit |
| tG(CCC)D | 2 | tRNA Gly |
| RDN | 3 | Ribosomal RNA subunits |
| YDL189W | 10 | R3H Domain Protein |
| CPA1 | 4 | ARG Biosynthesis |
| ADE16 | 2 | Adenine Biosynthesis |

For this data table, suppressors were recovered multiple times. The first column gives the gene or ORF name. The second gives the number of independent times this gene was recovered in the suppressor screen. The third column gives a brief description of the gene products of the high-copy suppressor genes.

Our genetic studies of the two yeast genes encoding PASK have helped establish a framework for understanding the biological role of this enzyme. Yeast cells without both enzymes are significantly impeded in vegetative growth when the cells are supplied with sub-optimal sources of sugar. Since seven of the eleven relevant high-copy suppressors—and as many as nine—encode products relating to RNA metabolism or translation, we conclude that PASK is involved in protein synthesis. Moving forward with this observation we prepared a dominant negative form of the human PASK enzyme in which a conserved lysine residue located within the ATP-binding region of the catalytic domain was mutated to arginine (designated K1028R). Baculovirus-expressed K1028R is completely inactive with respect to both autophosphorylation and trans-phosphorylation of the AMARA peptide. An expression vector encoding the K1028R variant of human PASK was transfected into cultured Rat-1 cells. Stable transformants were isolated and evaluated by western blotting using anti-hPASK antibodies. Two cell lines were chosen for further study, one expressing an intermediate level of the K1028R variant of PASK (designated KRint), and another expressing a higher level of the inactive enzyme (designated KRhi). The growth rate of the KRint cell line was slightly slower than that of Rat-1 cells that had been transfected with an empty expression vector. The KRhi cells doubled much more slowly, roughly 25% of the growth rate of control cells.

The KRhi cells were also observed to be substantially larger than control cells when viewed by light microscopy. Following this observation, FACS experiments were conducted to measure both the size and DNA content of log phase KRhi, KRint and control cells. The size distribution of KRhi cells was substantially different from both the KRint and control cells. More dramatic differences were observed in measurements of DNA content. KRhi cells display a bi-modal DNA contcorresponding to 2N and 4N the diploid DNA content of control Rat-1 cells. These observations are consistent with images of DAPI-stained cells. The nuclei of KRhi cells are considerably larger than those of control Rat-1 cells. In summary, these studies indicate that high levels of expression of a dominant-negative form of PASK slows the mitotic growth of Rat-1 cells and leads to a concomitant increase in both cell size and DNA content.

Our identification of a link between PASK—implicated in translational regulation by yeast genetics—and cell size control has a striking parallel to results of Thomas and colleagues [26]. By conditionally eliminating the 40S ribosomal protein S6 in adult mouse liver tissue, the Thomas laboratory has provided compelling evidence that lesions in the translation apparatus differentially affect mitotic growth as compared with cell size. Hepatocytes deficient in the S6 protein are unable to divide mitotically subsequent to hepatectomy. By contrast, when experimental animals are starved, these same S6-deficient hepatocytes are able to increase in cell size in response to re-feeding. Indeed, entire liver mass expands similarly in control and S6-deficient tissue in response to re-feeding. The very surprising and compelling observations of Thomas and colleagues reveal a fundamental difference between growth in cell size and mitotic growth in translationally-compromised hepatocytes.

The observations reported by Thomas and colleagues are consistent with emerging evidence that the genes encoding certain translation initiation factors are able to contribute to the transformed phenotype of cultured mammalian cells. The most compelling evidence that dysregulation of translation can foster transformation has come from studies of the 5' cap-binding factor eIF4E. Overexpression of this translation initiation factor has been shown to directly induce malignant transformation of NIH-3T3 cells [27]. Additional evidence indicating that enhancement of translation initiation can foster the transformed phenotype has come from studies of eIF4E expression levels in human tumors. As reviewed by Clemens and Bommer [28] and DeBendetti and Harris [29], eIF4E levels are significantly elevated in many solid tumors and tumor cell lines. The most pronounced increases in eIF4E expression have been found in breast cancer tissues, and head and neck squamous cell carcinomas [30–34]. Although evidence favoring the role of enhanced translation in the formation of human tumors is strongest in the case of eIF4E, elevated levels of mRNAs encoding eIF4A and eIF4G have also been detected in melanoma and squamous cell lung carcinoma tumors [35, 36]. Finally, the p48 subunit of eIF3 has been identified as the protein encoded by the int-6 gene, which is a site of frequent integration in the mouse genome by mouse mammary tumor virus [37].

Extensive mechanistic studies have resolved the biochemical functions of both positively- and negatively-acting translation initiation factors. The activity of the eIF4E cap binding factor is negatively regulated by proteins designated eIF4E binding proteins (4E-BPs). As reviewed by Raught and Gingras [38], both eIF4E and 4E-BPs are regulated by phosphorylation. The MAP kinase pathway (growth factor regulated), TOR pathway (growth factor regulated) and p38 pathway (stress regulated) have all been implicated in the phosphorylation of 4E-BPs. When phosphorylated, the 4E-BPs are released from eIF4E, allowing the cap binding protein to interact with eIF4G, form a stable interaction with 5' cap structures, and enhance the efficiency of translation initiation. Most components of this translational regulatory complex have been shown to be cytoplasmic and many tend to be enriched in the perinuclear region of mammalian cells [39]. Notably, PASK is identically distributed as assayed by immunohistochemical staining of cultured mammalian cells. In sum, these data indicate PASK can act by directly regulating the activity of specific translation initiation factors.

Biophysical studies of the PASK enzyme. In parallel with the functional studies of PASK, we undertook NMR-based studies of the structure, dynamics and ligand binding of the PAS domains of this protein. Our goals were two-fold: to determine if these domains are structurally homologous to other members of the PAS domain family and if so, to investigate whether they are capable of binding small molecule ligands in a similar manner.

Given the requirement for large (10–100 mg) quantities of soluble, isotopically-labeled protein for NMR studies, our first step was to optimize expression of PAS-containing constructs in bacterial systems. To this end, we used secondary structure prediction methods [40] to identify PAS domains from the primary amino acid sequence of PASK and design constructs that avoided having termini within secondary structure elements. These were cloned into a series of "parallel" expression vectors optimized for ease of cloning and expression [41] to rapidly generate a group of plasmids that can use bacteriophage T7-based systems to express the PAS fragments as C-terminal fusions to several partner proteins. As SDS-PAGE analysis identified several soluble fragments of PAS-A, we initially concentrated our attention on those.

We evaluated soluble fragments of PAS-A for their suitability for NMR studies by using a rapid NMR-based screening method [42, 43]. This approach is based on 2D $^{15}N/^{1}H$ HSQC spectra of $E.\ coli$ cell extracts from uniformly $^{15}N$-labeled cultures that have overexpressed proteins of interest. For proteins overexpressed at the levels we typically observe from T7-promoter driven systems, the high abundance of these proteins in the extract ensures that signals in these spectra are exclusively derived from the protein of interest. From these spectra, we can qualitatively estimate the number of residues in random coil conformations from the amide proton chemical shift dispersion, which is typically poor for unfolded proteins (7.8–8.4 ppm) as compared to folded proteins (6–10 ppm). As no protein purification is required, and these spectra can be acquired in 15–60 minutes on a 500 MHz NMR instrument, this method provides a quick assessment of folding and project feasibility at an early stage. Using this approach for a series of C-terminal deletion constructs of the PAS-A domain, we identified residues 131–237 as a minimal folding unit for this domain.

Having identified a well-folded PAS-A fragment that included residues 131–237, we began structural studies of this domain. Using size exclusion chromatography and $^{15}$N relaxation measurements, we established that this fragment was monomeric and thus could use standard triple resonance approaches to obtain $^{25}$N, $^{13}$C and $^{1}$H chemical shift assignments. As several reviews of these methods are available [44, 45], we will briefly survey this approach here. All of the NMR experiments were run on 1 mM samples of uniformly $^{15}$N or $^{15}$N/$^{13}$C labeled PAS-A using 500 and 600 MHz NMR spectrometers. Backbone chemical shift assignments were based on 3D HNCACB, CBCA(CO)NH, HNCO and HNHA spectra. Sidechain assignments for non-aromatic residues were obtained from 3D H(CCO)NH-TOCSY, (H)C(CO)NH-TOCSY and HCCH-TOCSY methods. Stereospecific assignments of Val and Leu methyl groups were based on constant time $^{13}$C/$^{1}$H spectra acquired on a uniformly 10% $^{13}$C-labeled sample [46]. Proton chemical shift assignments for the ring systems of the nine aromatic amino acids were based on 2D NOESY, DQF-COSY and TOCSY spectra recorded on an unlabeled PAS-A sample in 99.9% D$_2$O. Using this combination of methods, we obtained virtually complete chemical shift assignments for PAS-A.

Using these assignments, we determined the solution structure of PAS-A from the following information. Distance restraints were obtained from two isotope-edited 3D NOESY experiments ($^{15}$N- and $^{15}$N,$^{13}$C-edited [47]; $\tau_m$=150 ms) run on a uniformly $^{15}$N$^{13}$C sample in 90% H$_2$O: 10% D$_2$O and a 2D NOESY spectrum ($\tau_m$=120 ms) of an unlabeled sample in 99.9% D$_2$O. NOE peak intensities were qualitatively interpreted into three distance classes, accounting for chemical shift degeneracy [48]. Restraints on the backbone dihedral angles φ and ψ were derived from analyses of backbone $^{1}$H, $^{15}$N and $^{13}$C chemical shifts using the program TALOS [49] with minimum bounds of ±30°. Hydrogen bond restraints were derived from qualitative analyses of $^{2}$H exchange data, defining protected amides as those with significant protonation after 1 hour in 99.9% D$_2$O at pH 6.5, 25° C. Structures were generated with a standard simulated annealing protocol in CNS [50] using 515 manually assigned NOE-based distance restraints, 116 dihedral angle restraints and 48 hydrogen bond restraints. These structures were subsequently refined using an ambiguous NOE protocol as implemented in the ARIA enhancement of CNS [51]. Using ARIA-based interpretation of the 2D and 3D NOE spectra, we increased the number of interproton distance restraints from 515 to 2520. Furthermore, 61 $^{15}$N/$^{1}$H residual dipolar coupling restraints were added based on measurements made on a sample of PAS-A in a suspension of 10 mg/mL Pf1 filamentous bacteriophage [52].

We generated a group of 20 structures from this information with low total energy and few violations of experimental restraints. The high precision of these structures is indicated in the low backbone r.m.s. deviation of individual structures to the mean: 0.44±0.08 Å for residues located outside the Fα/FG region. This precision is typical of structures with a high average number of restraints per residue, as we have here (~25 restraints/residue). Most sidechains within the core of the protein are also well defined, with an r.m.s. deviation of 0.95±0.12 Å. Comparing these structures to those of other PAS domains [53–56] show that all have a similar global α/β fold, with a backbone r.m.s. deviation of 1.2–1.5 Å for residues in the β-sheet and N-terminal Cα, Dα and Eα helices.

Comparison of PAS domain structures reveals a key difference between the PAS-A domain of PASK and other PAS domains. In contrast to the long Fα helix observed in other structures, this helix and the subsequent FG loop are significantly disordered in PASK. This is consistent with our observations that signals from these regions were attenuated or missing in several of the spectra used for backbone chemical shift assignment. To investigate this further, we measured $^{15}$N relaxation rates to characterize the backbone dynamics of PAS-A. $^{15}$N T$_1$, T$_2$ and heteronuclear $^{15}$N{$^{1}$H} NOE values were determined using standard $^{15}$N/$^{1}$H HSQC-based experiments [57] and analyzed with a reduced spectral density function mapping approach [58, 59]. These results provide an experimental measurement of flexibility of the protein backbone on several timescales. Most of the protein is well ordered, as judged by the relatively uniform J values in residues in the Aβ-Dα and Gβ-Iβ secondary structure elements. However, the region between Eα and Gβ shows increased J(0.87Φ$_H$) and J$_{eff}$(0) values, consistent with increased flexibility on the nanosecond and millisecond timescales. This contrasts with $^{15}$N relaxation measurements on other PAS domains[55], which do not show any unusual flexibility in any secondary structure elements.

Based on our studies to this point, two lines of evidence pointed to the possibility that the PAS-A domain was capable of binding small ligands. First, the combination of structural and dynamic data clearly demonstrates the flexibility of the Fα and FG regions. Both of these regions are intimately involved in PAS/ligand interactions as shown in the structure of the FixL PAS domain bound to heme [56]. If PAS-A binds ligands in an induced fit manner, it is reasonable that these regions will be flexible in the absence of compound. Second, structure-based alignments show that key positions [60] in PAS-A are occupied by amino acids that may allow small molecules to bind in the core of this domain. These same positions are occupied by large hydrophobes in PAS domains that bind small ligands (PYP [53]) or no ligands (HERG [54]), effectively filling the central core. In contrast, FixL has two glycines in these positions to facilitate binding of the large heme ligand [56]. In PASK these sites are taken by amino acids that may similarly allow access into the core of the domain, due to their small size (Cys) or conformational preferences (Ile).

To directly investigate the ligand-binding capability of the PAS-A domain, we used NMR-based methods to screen a small library of synthetic organic compounds. This library consisted of approximately 150 compounds with formula weights between 200–300Da. Compounds were screened by adding groups of 5 (500 μM each) into samples of uniformly $^{15}$N-labeled protein (250 μM) and monitoring ligand-induced conformational changes in PAS-A by recording $^{15}$N/$^{1}$H HSQC spectra on these samples. If significant chemical shift changes were observed in these multiligand samples, we deconvoluted the contribution of each by examining the shifts of each ligand individually in new samples. In this manner, we identified eight compounds that bound PAS-A with K$_d$ values (measured by NMR) below 1 mM.

Spectra showing the chemical shift changes caused by the tightest binding of these compounds were determined. These data show that titrating this compound into a PAS-A sample leads to chemical shift changes in a limited number of residues that cluster in a region that is highly analogous to the heme-binding site of FixL [56].

We have obtained structure/activity relationship (SAR) information by examining the binding characteristics of structurally related compounds. For example, compound #134 has a bibenzyl architecture, a common feature of many protein-binding ligands [61, 62]. Comparing this ligand to other bibenzyl compounds in the library establishes the importance of a hydroxyl group located in the ethylene linker (Table 5). This information is used to guide construction of secondary libraries screened to improve the affinity and specificity of binding to PAS targets.

TABLE 5

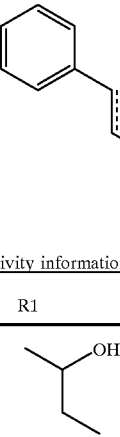

Structure-activity information on PAS-A binding compounds.

| compound | R1 | R2 | $K_d$ |
|---|---|---|---|
| #134 | 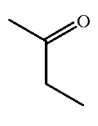 —OH | —H | ~100–200 µM |
| #130 | =O | —CH$_3$ | (>5 mM) |
| #133 |  | —H | (>5 mM) |

Comprehensive biochemical HTS for identifying specific, small molecule activators and inhibitors of PASK. We have adapted PASK protein binding assays, such as kinase and NMR-based assays, to high throughput screening (HTS). A compound collection initially consisting of roughly 350,000 drug-like chemicals has been collected, organized and extensively characterized in over 100 independent HTS assays. Such efforts have enabled the discovery of a large number of chemicals that potently and selectively modulate the activities of a broad range of polypeptide targets. The compound library has produced numerous drug entities that, following extensive optimization by medicinal chemistry, are in various phases of clinical and pre-clinical testing.

PASK HTS kinase assays identify both agonists and antagonists of the catalytic ability of the enzyme to phosphorylate the AMARA peptide. Our evidence indicates that the PASK PAS domains function as molecular sensors, negatively regulating the enzyme under conditions that are susceptible to depression in response to the appropriate intracellular signal. This parallels the AMPK system, which uses a regulatory domain and two negatively acting subunits to repress catalytic activity and simultaneously serve as the sensing device that monitors intracellular AMP/ADP-ATP ratios [4]. PAS domains have been reported to act as biosensors in studies of the aryl hydrocarbon receptor [73], photoactive yellow protein of the phototrophic bacterium *E. halophila* [74] and the bacterial Aer [75] and FixL [76] proteins.

One HTS assay kinase assay we employ is a robust and simple, non-radioactive chemiluminescent assay that measures the ability of the human enzyme to phosphorylate a biotinylated derivative of the AMARA peptide. The enzyme is expressed in baculovirus and purified by affinity and ion-exchange chromatography under routine conditions. Assay buffer is composed of 20 mM Tris-HCl, pH 7.5, 10 mM MgCl$_2$, 2 mM EGTA, 0.1% NP-40, 0.5 mM benzamidine, 1 mM NaF and 10 mM DTT. Enzyme is added to this buffer at a concentration determined to be in the linear range of activity (long per microtiter plate well). For the most robust and sensitive kinase assay, we use an ATP concentration matching the $K_m$ for PASK (2.5 mM). After dispensing 80 µl of the enzyme/buffer mix per well in Costar 96-well microtiter plates (coated with Neutravidin at 0.5 mg/ml at room temperature for 2 hr), 10 µl of test compounds is added at a final concentration of 1 µM compound. Compounds are diluted in DMSO from master plates stored in DMSO at 10 mM. Following compound addition, the reactions are initiated by addition of 10 µl of biotinylated AMARA peptide and ATP such that the final concentration of substrate and ATP are 1 mM and 2.5 mM respectively. Instrumentation for the addition of buffer/enzyme mix, diluted compounds and substrate/ATP is the Robbins Hydra 96 multipipette. Following brief shaking on a microtiter plate shaker (Lab-Line Instruments), plates are incubated for 1 hr at room temperature, washed 3× with distilled H$_2$O using a LABTEK 96-well wash, and applied with 100 µl per well of antibody buffer. The primary antibody is a mouse monoclonal antibody specific to the phosphorylated AMARA peptide (Pan Vera). The secondary antibody is an HRP-labeled rabbit, anti-mouse antibody (New England Biolabs). The final antibody buffer mix contains 2% BSA in PBS. After antibody addition the plates are briefly shaken, incubated at room temperature for 1 hr and washed 3× with H$_2$O. Reactions are developed by addition of 100 µl of Super Signal substrate (Pierce) and read calorimetrically using a Wallac Victor2, 1420 Multilabel Counter. Target specificity is confirmed by comparative assays with control non-PASK protein kinases.

Compounds showing good dose response curves, corresponding to potent agonistic or antagonistic activity, are tested against six versions of the human PASK enzyme. Three of the enzyme samples represent the intact protein in: (i) its native state as purified from baculovirus; (ii) its activated state following autophosphorylation; (iii) and its inactivated state following treatment with lambda phosphatase. Concomitant experiments are conducted using the amino-terminal truncated enzyme lacking its two PAS domains, again using the native enzyme as well as the phosphorylated and dephosphorylated derivatives. This secondary level of follow-up distinguishes between compounds that act on the kinase domain versus those that require the PAS domains for either stimulatory or inhibitory activity. Compounds from the HTS screen are evaluated by HPLC, mass spectrometry and NMR spectroscopy, not only of the starting compound, but also of analogs produced as a means of establishing a structure activity relationship (SAR) between the compound and its ability to either inhibit or stimulate PASK.

High throughput NMR-based protein/ligand screening. Two important facets of NMR-based protein/ligand screens are the size and scope of the compound libraries that are being used. One type of library we use is a "directed" library, consisting of a small (100–200) number of compounds whose structures are based on common structural elements of PAS-binding ligands, including biological cofactors (heme, NADH, FMN, $FADH_2$), chromophores (hydroxycinnaminic acid), environmental toxins (tetrachlorodibenzodioxin [TCDD]), etc. These have several features in common, including planarity, conjugation and limited charge at neutral pH. Chemical databases are searched with these criteria, starting with substructures that match common frameworks of PAS ligands. Additional geometric criteria are obtained from observations that protein-binding ligands are inherently biased towards certain chemical architectures [61, 79]. Many of these architectures are aromatic-rich and include the general structures of several PAS-binding ligands including PASK-binding compound #134 (Table 5). We also screen larger libraries (1000–2000 compounds) that are designed to cover a wider range of chemical structures while still taking advantage of the observed biases of protein-binding ligands [61, 79]. Compounds in this library are also chosen with an emphasis towards later use in synthetic approaches, with relatively low formula weight (100–200Da) and composition of functional groups.

A wide variety of NMR-based methods are available to rapidly screen libraries of small compounds for binding to protein targets [82]. We primarily use protein-based screening methods, which are well suited for PAS domains given their small size (10–15 kDa) and the structural information obtained from the studies outlined above. As demonstrated with PAS-A, we screen using isotopically labeled protein and unlabeled ligands, using HSQC-type experiments to selectively observe protein signals in the presence of excess ligand. Compounds are maintained as 1M stocks in deuterated DMSO, and protein samples checked to ensure that DMSO does not bind with any significant affinity. Samples of $^{15}N/^{13}C$-methyl labeled protein (250 $\mu$M) are mixed with 3–10 compounds at 1 mM each, which is sufficient to find ligands with weak (millimolar) dissociation constants. Protein chemical shifts are recorded using $^{13}C/^{1}H$ HSQC as our primary method, complemented by $^{15}N/^{1}H$ HSQC. Spectra from ligand-containing solutions are compared to those from ligand-free samples, calculating chemical shift changes with the minimum chemical shift difference method [83]. Where significant changes are observed, we deconvolute the binding of each ligand in the mixture by examining new samples with single protein/ligand mixtures. Compounds that demonstrate binding are titrated into a sample of $^{15}N$-labeled protein to measure dissociation constants, which can be measured by NMR if the complex is in fast exchange ($K_d$>10 $\mu$M).

Screening throughput of this method can exceed 1000 compounds per day for the initial screen: 15 minutes per sample (10' experimental, 5' sample manipulation) and 10 ligands/sample. PAS-binding compounds identified in this screen are evaluated for their ability to modulate PASK function in vitro using the previously described peptide phosphorylation assay. Compounds are checked for effects on both full length and truncated versions of PASK containing only the kinase domain to ensure that any modulatory action is mediated through the PAS domains.

We use several sources of structure-activity relationship information available from the first round of screening to generate small secondary libraries that we screen to find compounds with higher affinity. As shown above, comparisons of the affinity of structurally-related compounds identify positions on ligands that are essential for binding. Additionally, comparisons of the chemical shift changes caused by related ligands rapidly identify the relative orientation of protein/ligand complexes [85], potentially identifying sites on these ligands that may be amenable to modification as an avenue to increase affinity. The combination of these approaches allows us to design libraries that are simple modifications of ligands from the first screen.

An alternative approach that generates more drastically altered ligands for the second library is the SAR-by-NMR method [86]. We conduct two screens through the primary library with the goal of finding two ligands that bind at adjacent sites on the protein structure. This is achieved by a first screen as previously discussed, followed by a second screen through the library in the presence of saturating concentrations of a ligand identified by the first screen. Through the use of protein-directed NMR experiments such as the $^{13}C/^{1}H$ HSQC, one can readily identify compounds from the second screen that bind at an adjacent site to the first compound. We then obtain a structure of the ternary complex of the protein bound to both ligands. This is achieved by obtaining similar structural information as used for the PAS-A structure determination complemented by intermolecular distance restraints using isotope-filtered, edited 3D NOE experiments [87] that provide the selective observation of NOEs between isotopically-enriched proteins and non-enriched ligands. Guided by this structure, we identify sites on each ligand that can be used to generate a linker between the two compounds in the expectation that the linked compound will have enhanced affinity over the two separate compounds. Libraries are constructed from this information using a series of linkers with variable length and flexibility. We screen these secondary library compounds for binding to the PAS-A and PAS-B domains as described above.

Phosphorylation Screening. An alternative strategy to identify PASK substrates follows methods developed by Hunter and colleagues for the identification of protein kinase substrates by expression screening with solid-phase phosphorylation. This method, termed "phosphorylation screening," represents an adaptation of classical methods of expression screening using bacteriophage lambda. Hunter and colleagues have used this approach to identify known and novel substrates for the Erk1 [65] and Cdk2 [66] protein kinases.

Yeast cDNA are cloned into the λGEX5 vector developed by Hunter and colleagues. This bacteriophage lambda vector contains a plasmid sequence between two NotI sites, consisting of a ColE1 origin, the ampicillin resistance gene, and a GST gene followed by a small "stuffer" sequence to be replaced by cDNA inserts. Compared with the original λgt11 vector, the λGEX5 vector provides three important advantages. First, clones encoding polypeptides phosphorylated by PASK can be rapidly converted into plasmid clones by excision rescue without purifying cDNA fragments. Second, rescued plasmids can be directly utilized not only for cDNA sequencing but also for expression of GST fusion proteins for further characterization. Finally, GST, the N-terminal fusion partner of the recombinant product expressed by λGEX5, is highly soluble, easy to purify by GSH-agarose chromatography, and much smaller than the β-galactosidase component of the fusion proteins expressed by λgt11.

Expression libraries are screened according to the methods of Hunter and Fukunaga [65] using human PASK expressed in baculovirus. Prior to the phosphorylation step of the assay, filter lifts are incubated in the presence of unlabelled ATP as a means of reducing the frequency of isolating clones whose products have either autophosphorylating or ATP-binding activity. Highly purified, autophosphorylated (activated) human PASK is added with [γ-$^{32}$P]ATP in optimal buffer conditions. Following incubation, the filters are washed and exposed to X-ray film to identify plaques expressing polypeptide substrates for PASK. Optimization strategies outlined by Hunter and Fukunaga are followed to expedite completion of a successful screen. After retrieving nitroceluose lifts bearing lambda-expressed proteins, filters are exposed to 6M urea followed by sequential dilution and ultimate removal of the urea. This approach helps solubilize over-expressed proteins which are often restricted to inclusion bodies. In the case of expression cloning of eukaryotic transcription factors, inclusion of the urea solubilization step substantially enhanced signal to noise ratios [67].

Positive plaques are isolated, from which encoding plasmids are excised and sequenced. Particularly interesting substrate proteins are further studied to identify precise sites of phosphorylation using GST-fusion proteins expressed and purified from E. coli. Finally, individual serine and threonine sites are altered by site directed mutagenesis followed by reintroduction of the mutant on a plasmid in a strain deleted for the chromosomal copy of the gene so as to facilitate further biochemical and biological assays.

In addition to phosphorylation screening, we employ an entirely different approach described by Kirschner and colleagues [68–70]. This approach also relies on the screening of cDNA libraries, yet in this case the assay is conducted on pools of in vitro translation products. In brief, a cDNA library is prepared from poly(A)+ yeast RNA cloned into the pCS2+ vector [71]. cDNAs larger than 0.5 kb is ligated directionally into pCS2+ and electroporated into competent E. coli cells. The pCS2+ plasmid contains regulatory sequences for coupled transcription/translation immediately upstream from the directionally cloned cDNA insert site, thus facilitating TNT-mediated transcription/translation in reticulocyte lysates. We follow the methods of Kirshner and colleagues to simultaneously at express pools of ~100 cDNA clones, typically resulting in the synthesis of 15–30 $^{35}$S-labeled polypeptides. These pools of in vitro translated protein will subsequently be incubated with baculovirus-expressed PASK under optimal conditions for its enzymatic activity. Following phosphorylation with cold ATP, the $^{35}$S-labeled protein pools are run on SDS-PAGE gels followed by autoradiographic imaging. Control reactions are conducted in the absence of PASK such that pooled samples can be compared side-by-side on SDS-PAGE gels. Proteins phosphorylated by PASK are provisionally identified by a shift in their electrophoretic mobility. Pools containing cDNA capable of expressing PAS-kinase modified polypeptides are de-convoluted in order to identify relevant cDNAs and their encoded polypeptides.

Protocol for high throughput PASK autophosphorylation assay.

A. Reagents

Neutralite Avidin: 20 μg/ml in PBS.

kinase: $10^{-8}$–$10^5$M PASK kinase domain at 20 μg/ml in PBS.

substrate: $10^{-7}$–$10^{-4}$M biotinylated PASK substrate at 40 μg/ml in PBS.

Blocking buffer: 5% BSA, 0.5% Tween 20 in PBS; 1 hour at room temperature.

Assay Buffer: 100 mM KCl, 10 mM MgCl$_2$, 1 mM MnCl$_2$, 20 mM HEPES pH 7.4, 0.25 mM EDTA, 1% glycerol, 0.5% NP-40, 50 mM BME, 1 mg/ml BSA, cocktail of protease inhibitors.

[$^{32}$P]μ-ATP 10× stock: 2×$10^{-5}$M cold ATP with 100 μCi [$^{32}$P]μ-ATP. Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.

B. Preparation of Assay Plates

Coat with 120 1 μl of stock N Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 40 μl biotinylated substrate (2–200 pmoles/40 ul in assay buffer)

Add 40 μl kinase (0.1–10 pmoles/40 ul in assay buffer)

Add 10 μl compound or extract.

Add 10 μl [$^{32}$P]γ-ATP 10×stock.

Shake at 25° C. for 15 minutes.

Incubate additional 45 minutes at 25° C.

Stop the reaction by washing 4 times with 200 μl PBS.

Add 150 μl scintillation cocktail.

Count in Topcount.

D. Controls for All Assays (Located on Each Plate)
a. Non-specific binding
b. cold ATP at 80% inhibition.

Protocol for High Throughput PASK PAS Domain—ligand Binding Assay.

A. Reagents

Neutralite Avidin: 20 μg/ml in PBS.

Blocking buffer: 5% BSA, 0.5% Tween 20 in PBS; 1 hour at room temperature.

Assay Buffer: 100 mM KCl, 20 mM HEPES pH 7.6, 1 mM MgCl$_2$, 1% glycerol, 0.5% NP-40, 50 mM b-mercaptoethanol, 1 mg/ml BSA, cocktail of protease inhibitors.

$^{33}$P PASK polypeptide 10×stock: $10^{-8}$–$10^{-6}$M "cold" PASK PAS domain supplemented with 200,000–250,000 cpm of labeled PASK (Beckman counter). Place in the 4° C. microfridge during screening.

Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVO$_3$ (Sigma #S-6508) in 10 ml of PBS.

Ligand: $10^{-7}$–$10^{-5}$M biotinylated ligand in PBS.

B. Preparation of Assay Plates

Coat with 120 μl of stock N-Avidin per well overnight at 4° C.

Wash 2 times with 200 μl PBS.

Block with 150 μl of blocking buffer.

Wash 2 times with 200 μl PBS.

C. Assay

Add 40 μl assay buffer/well.

Add 10 μl compound or extract.

Add 10 μl $^{33}$P-PASK polypeptide (20–25,000 cpm/0.1–10 pmoles/well=$10^{-9}$–$10^{-7}$ M final conc).

Shake at 25° C. for 15 minutes.

Incubate additional 45 minutes at 25° C.

Add 40 µM biotinylated ligand (0.1–10 pmoles/40 µl in assay buffer)

Incubate 1 hour at room temperature.

Stop the reaction by washing 4 times with 200 µM PBS.

Add 150 µM scintillation cocktail.

Count in Topcount.

D. Controls for All Assays (Located on Each Plate)
   a. Non-specific binding
   b. Soluble (non-biotinylated ligand) at 80% inhibition.

Literature cited.

1. Hanks, S. K., et al. Science, 1988. 241(4861):42–52.
2. Dale, S., et al. FEBS Letters, 1995. 361(2–3):191–5.
3. Stein, S. C., et al. Biochemical J, 2000. 345(Pt 3):437–43.
4. Hardie, D. G., et al. Annual Review of Biochemistry, 1998. 67:821–55.
5. Crute, B. E., et al. J Biological Chemistry, 1998. 273(52):35347–35354.
6. Woods, A., et al. Molecular & Cellular Biology, 2000. 20(18):6704–6711.
7. Hampsey, M., Yeast, 1997. 13(12):1099–133.
8. Sikorski, R. S., et al. Genetics, 1989. 122(1):19–27.
9. Scriver, S. C., et al. *The Metabolic Basis of Inherited Disease (6th ed)*. 1989:ch. 13.
10. Boles, E., et al. European J Biochemistry, 1994. 220(1):83–96.
11. Mylin, L. M., et al. Genetics, 1994. 137(3):689–700.
12. Cartwright, J. L., et al. J Biological Chemistry, 1999. 274(13):8604–10.
13. Safrany, S. T., et al. J Biological Chemistry, 1999. 274(31):21735–40.
14. Chuang, R. Y., et al. Science, 1997. 275(5305):1468–71.
15. Jamieson, D. J., et al. Molecular Microbiology, 1991. 5(4):805–12.
16. Jamieson, D. J., et al. Nature, 1991. 349(6311):715–7.
17. Dunckley, T., et al. EMBO Journal, 1999. 18(19):5411–22.
18. Chu, S., et al. Rna, 1997. 3(4):382–91.
19. Lee, J. Y., et al. Molecular & Cellular Biology, 1991. 11(2):721–30.
20. Mendenhall, M. D., et al. Nucleic Acids Research, 1988. 16(17):8713.
21. Venema, J., et al. Annual Review of Genetics, 1999. 33:261–311.
22. Grishin, N. V., Trends in Biochemical Sciences, 1998. 23(9):29–30.
23. Lim, A. L., et al. J Biological Chemistry, 1996. 271(19):11400–11409.
24. Werner, M., et al. Cell, 1987. 49(6):805–13.
25. Wang, Z., et al. J Biological Chemistry, 1999. 274(53):37565–74.
26. Volarevic, S., et al. Science,,2000. 288(5473):2045–7.
27. Lazaris-Karatzas, A., Nature, 1990. 345(6275):544–7.
28. Clemens, M. J., et al. International J Biochem & Cell Biol, 1999. 31(1):1–23.
29. De Benedetti, A., et al. International J Biochem & Cell Biol, 1999. 31(1):59–72.
30. Nathan, C. A., et al. Oncogene, 1997. 15(9):1087–94.
31. Nathan, C. A., et al. Oncogene, 1997. 15(5):579–84.
32. Li, B. D., et al. Cancer, 1997. 79(12):2385–90.
33. Miyagi, Y., et al. Cancer Letters, 1995. 91(2):247–52.
34. Anthony, B., et al. International J Cancer, 1996. 65(6):858–63.
35. Eberle, J., et al. International J Cancer, 1997. 71(3):396–401.
36. Brass, N., et al. Human Molecular Genetics, 1997. 6(1):33–9.
37. Asano, K., et al. J Biological Chemistry, 1997. 272(38):23477–80.
38. Raught, B., et al. International J Biochem & Cell Biology, 1999. 31(1):43–57.
39. Liang, L., et al. Development, 1994. 120(5):1201–11.
40. Cuff, J. A., et al. Bioinformatics, 1998. 14:892–893.
41. Sheffield, P., Protein Expression and Purification, 1999. 15:34–39.
42. Gronenborn, A. M., et al Protein Science, 1996. 5:174–177.
43. Huth, J. R., et al. Protein Science, 1997. 6:2359–2364.
44. Clore, G. M., et al. Trends Biotechnol., 1998. 16:22–34.
45. Sattler, M., et al. Progr Nucl Magnetic Resonance Spectrosc, 1999. 34:93–158.
46. Neri, D., et al. Biochemistry, 1989. 28:7510–7516.
47. Pascal, S. M., et al. J Magnetic Resonance B, 1994. 103:197–201.
48. Fletcher, C. M., et al. J Biomolecular NMR, 1996. 8:292–310.
49. Cornilescu, G., et al. J Biomolecular NMR, 1999.13:289–302.
50. Brünger, A. T., et al. Acta. Cryst., 1998. D54:905–921.
51. Nilges, M., et al. Progr Nucl Magnetic Resonance Spectrosc, 1998.32:107–139.
52. Hansen, M. R., et al. Nature Structural Biology, 1998. 5(12):1065–1074.
53. Borgstahl, G. E. O., et al. Biochemistry, 1995. 34:6278–6287.
54. Cabral, J. H. M., et al. Cell, 1998. 95:649–655.
55. Düx, P., et al. Biochemistry, 1998. 37(37):12689–12699.
56. Gong, W., et al. Proc. Natl. Acad. Sci., 1998. 95:15177–15182.
57. Farrow, N. A., et al. Biochemistry, 1994. 33:5984–6003.
58. Bracken, C., et al. J Molecular Biology, 1999. 285:2133–2146.
59. Farrow, N. A., et al. J Biomolecular NMR, 1995. 6:153–162.
60. Pellequer, J. L., et al. Current Biology, 1999. 9(11):R416–8.
61. Fejzo, J., et al. Chemistry and Biology, 1999. 6:755–769.
62. Hajduk, P. J., et al. J Medicinal Chemistry, 2000. 43(21):3862–6
63. Kranz, J. E., et al. Proc. of the Natl. Acad. Sci. USA, 1990. 87(17):6629–33.
64. Koshland, D., et al. Cell, 1985. 40(2):393–403.
65. Fukunaga, R., et al. EMBO Journal, 1997. 16(8):1921–33.
66. Jiang, W., et al. Molecular Cell, 1998. 2(6):877–85.
67. Vinson, C. R., et al. Genes & Development, 1988. 2(7):801–6.
68. Stukenberg, P. T., et al. Current Biology, 1997. 7(5):338–48.
69. Lustig, K. D., et al. Methods in Enzymology, 1997. 283:83–99.
70. King, R. W., et al. Science, 1997. 277(5328):973–4.
71. Turner, D. L., et al. Genes & Development, 1994. 8(12):1434–47.
72. McKnight, S. L., et al. Science, 1982. 217(4557):316–24.
73. Rowlands, J. C., et al. Critical Reviews in Toxicology, 1997. 27(2):109–34.
74. Farber, G. K., Nature Structural Biology, 1998. 5(6):415–7.
75. Taylor, B. L., et al. Annual Review of Microbiology, 1999. 53:103–28.

76. Pellequer, J. L., et al. Curr Biol, 1999. 9(11):R416–8.
77. Wang, Z., et al. Structure, 1998. 6(9):1117–28.
78. Gum, R. J., et al. J Biological Chemistry, 1998. 273(25): 15605–10.
79. Hajduk, P. J., et al. J American Chemical Society, 2000. 122:7898–7904.
80. Matthews, S. J., et al. J Biomolecular NMR, 1993. 3:597–600.
81. Meiler, J., et al. J Biomolecular NMR, 2000. 16:245–252.
82. Hajduk, P. J., et al. Quarterly Reviews of Biophysics, 1999. 32 (3): 211–40.
83. Farmer, B. T. I., et al. Nature Structural Biology, 1996. 3:995–997.
84. Johnson, B. A., et al. J Biomolecular NMR, 1994. 4:603–614.
85. Medek, A., et al. J American Chemical Society, 2000. 122(6):1241–1242.
86. Shuker, S. B., et al. Science, 1996. 274:1531–1534.
87. Zwahlen, C., et al. J American Chemical Society, 1997. 119:6711–6721.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising an isolated polypeptide, said polypeptide:
   (a) comprising SEQ ID NO:2;
   (b) comprising residues 1–89 of SEQ ID NO:2 and sufficient to elicit a human PASK (SEQ ID NO:2)-specific antibody in a heterologous host;
   (c) consisting of about residues 131–237 of SEQ ID NO:2; or
   (d) consisting of about residues 341–439 of SEQ ID NO:2.

2. A composition according to claim 1, wherein the polypeptide comprises SEQ ID NO:2.

3. A composition according to claim 1, wherein the polypeptide comprises residues 1–89 of SEQ ID NO:2 and is sufficient to elicit a human PASK (SEQ ID NO:2)-specific antibody in a heterologous host.

4. A composition according to claim 1, wherein the polypeptide consists of about residues 131–237 of SEQ ID NO:2.

5. A composition according to claim 1, wherein the polypeptide consists of about residues 341–439 of SEQ ID NO:2.

6. A composition according to claim 1, wherein the polypeptide consists of residues 131–237 of SEQ ID NO:2.

7. A composition according to claim 1, wherein the polypeptide consists of residues 341–439 of SEQ ID NO:2.

8. A composition according to claim 1, further comprising ligand which binds the polypeptide.

9. A method of detecting polypeptide-ligand binding comprising the steps of:
   (a) incubating a composition according to claim 8 under conditions wherein the polypeptide binds the ligand; and
   (b) detecting the binding of the polypeptide to the ligand.

10. A method according to claim 9, wherein the composition further comprises a candidate modulator of the polypeptide-ligand binding.

11. A method according to claim 9, wherein the polypeptide comprises SEQ ID NO:2, the ligand is a substrate, the composition further comprises a nucleoside triphosphate, the binding effects phosphorylation of the substrate, and the detecting step comprises detecting the phosphorylated substrate.

12. A method according to claim 9, wherein the polypeptide consists of about residues 131–237 of SEQ ID NO:2 and the detecting step comprises detecting a change in NMR chemical shifts of the polypeptide and/or the ligand.

13. A method according to claim 9, wherein the polypeptide consists of about residues 341–439 of SEQ ID NO:2 and the detecting step comprises detecting a change in NMR chemical shifts of the polypeptide and/or the ligand.

* * * * *

SEQUENCE LISTING

```
<160> NUMBER OF SEQ ID NOS:  9

<210> SEQ ID NO 1
<211> LENGTH: 3972
<212> TYPE: DNA
<213> ORGANISM: human
<220> FEATURE:
<221> NAME/KEY: CDS
<222> LOCATION: (1)..(3969)

<400> SEQUENCE: 1 atg gag gac ggg ggc tta aca gcc ttt gaa gag gac cag aga tgc ctt      48
Met Glu Asp Gly Gly Leu Thr Ala Phe Glu Glu Asp Gln Arg Cys Leu
1               5                  10                  15 tcc cag agc ctc ccc ttg cca gtg tca gca gag ggc cca gct gca cag      96
Ser Gln Ser Leu Pro Leu Pro Val Ser Ala Glu Gly Pro Ala Ala Gln
            20                  25                  30 acc act gct gag ccc agc agg tcg ttt tcc tca gcc cac aga cac ctg     144
Thr Thr Ala Glu Pro Ser Arg Ser Phe Ser Ser Ala His Arg His Leu
        35                  40                  45 agc aga agg aat ggg ctt tcc aga ctc tgc cag agc agg aca gcg ctc     192
Ser Arg Arg Asn Gly Leu Ser Arg Leu Cys Gln Ser Arg Thr Ala Leu
    50                  55                  60 tct gaa gac aga tgg agc tcc tat tgt cta tca tca ctg gct gcc cag     240
Ser Glu Asp Arg Trp Ser Ser Tyr Cys Leu Ser Ser Leu Ala Ala Gln
65                  70                  75                  80 aat att tgt aca agt aaa ctg cac tgc cct gct gcc cct gag cac acg     288
Asn Ile Cys Thr Ser Lys Leu His Cys Pro Ala Ala Pro Glu His Thr
                85                  90                  95 gac ccg tcc gaa ccg cgg ggc agt gtg tcc tgc tgc tcc ctg ctg cgg     336
Asp Pro Ser Glu Pro Arg Gly Ser Val Ser Cys Cys Ser Leu Leu Arg
            100                 105                 110 gga ctg tcc tca ggg tgg tcc tca cct ctt ccg gcc cct gtg tgc         384
Gly Leu Ser Ser Gly Trp Ser Ser Pro Leu Leu Pro Ala Pro Val Cys
        115                 120                 125 aac cct aac aag gcc atc ttc acg gtg gat gcc aag acc aca gag atc     432
Asn Pro Asn Lys Ala Ile Phe Thr Val Asp Ala Lys Thr Thr Glu Ile
    130                 135                 140 ctg gtt gct aac gac aaa gct tgc ggg ctc ggg tac agc agc cag         480
Leu Val Ala Asn Asp Lys Ala Cys Gly Leu Leu Gly Tyr Ser Ser Gln
145                 150                 155                 160 gac ctg att ggc cag aag ctc acg cag ttc ttt ctg agg tca gat tct     528
Asp Leu Ile Gly Gln Lys Leu Thr Gln Phe Phe Leu Arg Ser Asp Ser
                165                 170                 175
```

```
gat gtg gtg gag gcc ctc agc gag gag cac atg gag gcc gac ggc cac     576
Asp Val Val Glu Ala Leu Ser Glu Glu His Met Glu Ala Asp Gly His
            180                 185                 190 gct gcg gtg gtg ttt ggc acg gtg gtg gac atc atc agc cgt agt ggg     624
Ala Ala Val Val Phe Gly Thr Val Val Asp Ile Ile Ser Arg Ser Gly
            195                 200                 205 gag aag att cca gtg tct gtg tgg atg aag agg atg cgg cag gag cgc     672
Glu Lys Ile Pro Val Ser Val Trp Met Lys Arg Met Arg Gln Glu Arg
            210                 215                 220 cgc cta tgc tgc gtg gtg gtc ctg gag ccc gtg gag agg gtc tcg acc     720
Arg Leu Cys Cys Val Val Val Leu Glu Pro Val Glu Arg Val Ser Thr
225                 230                 235                 240 tgg gtc gct ttc cag agc gat ggc acc gtc acg tca tgt gac agt ctc     768
Trp Val Ala Phe Gln Ser Asp Gly Thr Val Thr Ser Cys Asp Ser Leu
                245                 250                 255 ttt gct cat ctt cac ggg tac gtg tct ggg gag gac gtg gct ggg cag     816
Phe Ala His Leu His Gly Tyr Val Ser Gly Glu Asp Val Ala Gly Gln
                260                 265                 270 cat atc aca gac ctg atc cct tct gtg cag ctc cct cct tct ggc cag     864
His Ile Thr Asp Leu Ile Pro Ser Val Gln Leu Pro Pro Ser Gly Gln
            275                 280                 285 cac atc cca aag aat ctc aag att cag agg tct gtt gga aga gcc agg     912
His Ile Pro Lys Asn Leu Lys Ile Gln Arg Ser Val Gly Arg Ala Arg
            290                 295                 300 gac ggt acc acc ttc cct ctg agc tta aag ctg aaa tcc caa ccc agc     960
Asp Gly Thr Thr Phe Pro Leu Ser Leu Lys Leu Lys Ser Gln Pro Ser
305                 310                 315                 320 agc gag gag gcg acc acc ggt gag gcg gcc cct gtg agc ggc tac cgg    1008
Ser Glu Glu Ala Thr Thr Gly Glu Ala Ala Pro Val Ser Gly Tyr Arg
                325                 330                 335 gca tct gtc tgg gtg ttc tgc acc atc agt ggc ctc atc acc ctc ctg    1056
Ala Ser Val Trp Val Phe Cys Thr Ile Ser Gly Leu Ile Thr Leu Leu
                340                 345                 350 ccg gat ggg acc atc cac ggc atc aac cac agc ttc gcg ctg aca ctg    1104
Pro Asp Gly Thr Ile His Gly Ile Asn His Ser Phe Ala Leu Thr Leu
            355                 360                 365 ttt ggt tac gga aag acg gag ctc ctg ggc aag aat atc act ttc ctg    1152
Phe Gly Tyr Gly Lys Thr Glu Leu Leu Gly Lys Asn Ile Thr Phe Leu
370                 375                 380 att cct ggt ttc tac agc tac atg gac ctt gcg tac aac agc tca tta    1200
Ile Pro Gly Phe Tyr Ser Tyr Met Asp Leu Ala Tyr Asn Ser Ser Leu
385                 390                 395                 400 cag ctc cca gac ctg gcc agc tgc ctg gac gtc ggc aat gag agt ggg    1248
Gln Leu Pro Asp Leu Ala Ser Cys Leu Asp Val Gly Asn Glu Ser Gly
                405                 410                 415 tgt ggg gag aga acc ttg gac ccg tgg cag ggc cag gac cca gct gag    1296
Cys Gly Glu Arg Thr Leu Asp Pro Trp Gln Gly Gln Asp Pro Ala Glu
                420                 425                 430 ggg ggc cag gat cca agg att aat gtc gtg ctt gct ggt ggc cac gtt    1344
Gly Gly Gln Asp Pro Arg Ile Asn Val Val Leu Ala Gly Gly His Val
            435                 440                 445 gtg ccc cga gat gag atc cgg aag ctg atg gaa agc caa gac atc ttc    1392
Val Pro Arg Asp Glu Ile Arg Lys Leu Met Glu Ser Gln Asp Ile Phe
450                 455                 460 acc ggg act cag act gag ctg att gct gga ggc cag ctc ctt tcc tgc    1440
Thr Gly Thr Gln Thr Glu Leu Ile Ala Gly Gly Gln Leu Leu Ser Cys
465                 470                 475                 480 ctc tca cct cag cct gct cca ggg gtg gac aat gtc cca gaa gga agc    1488
Leu Ser Pro Gln Pro Ala Pro Gly Val Asp Asn Val Pro Glu Gly Ser
```

```
                       485                 490                 495
ctg cca gtg cac ggt gaa cag gcg ctg ccc aag gac cag caa atc act       1536
Leu Pro Val His Gly Glu Gln Ala Leu Pro Lys Asp Gln Gln Ile Thr
                500                 505                 510 gcc ttg ggg aga gag gaa cct gtg gca ata gag agc ccc gga cag gat       1584
Ala Leu Gly Arg Glu Glu Pro Val Ala Ile Glu Ser Pro Gly Gln Asp
                515                 520                 525 ctt ctg gga gaa agc agg tct gaa cca gtg gat gtg aag cca ttt gct       1632
Leu Leu Gly Glu Ser Arg Ser Glu Pro Val Asp Val Lys Pro Phe Ala
            530                 535                 540 tcc tgc gaa gat tct gaa gct cca gtc cca gct gag gat ggg ggc agt       1680
Ser Cys Glu Asp Ser Glu Ala Pro Val Pro Ala Glu Asp Gly Gly Ser
545                 550                 555                 560 gat gct ggc atg tgt ggc ctg tgt cag aag gcc cag cta gag cgg atg       1728
Asp Ala Gly Met Cys Gly Leu Cys Gln Lys Ala Gln Leu Glu Arg Met
                565                 570                 575 gga gtc agt ggt ccc agc ggt tca gac ctt tgg gct ggg gct gcc gtg       1776
Gly Val Ser Gly Pro Ser Gly Ser Asp Leu Trp Ala Gly Ala Ala Val
                580                 585                 590 gcc aag ccc cag gcc aag ggt cag ctg gcg ggg ggc agc ctc ctg atg       1824
Ala Lys Pro Gln Ala Lys Gly Gln Leu Ala Gly Gly Ser Leu Leu Met
                595                 600                 605 cac tgc cct tgc tat ggg agt gaa tgg ggc ttg tgg tgg cga agc cag       1872
His Cys Pro Cys Tyr Gly Ser Glu Trp Gly Leu Trp Trp Arg Ser Gln
                610                 615                 620 gac ttg gcc ccc agc ccc tct ggg atg gca ggc ctc tcg ttt ggg aca       1920
Asp Leu Ala Pro Ser Pro Ser Gly Met Ala Gly Leu Ser Phe Gly Thr
625                 630                 635                 640 cct act cta gat gag ccg tgg ctg gga gtg gaa aac gac cga gaa gag       1968
Pro Thr Leu Asp Glu Pro Trp Leu Gly Val Glu Asn Asp Arg Glu Glu
                645                 650                 655 ctg cag acc tgc ttg att aag gag cag ctg tcc cag ttg agc ctt gca       2016
Leu Gln Thr Cys Leu Ile Lys Glu Gln Leu Ser Gln Leu Ser Leu Ala
                660                 665                 670 gga gcc ctg gat gtc ccc cac gcc gaa ctc gtt ccg aca gag tgc cag       2064
Gly Ala Leu Asp Val Pro His Ala Glu Leu Val Pro Thr Glu Cys Gln
                675                 680                 685 gct gtc acc gct cct gtg tcg tcc tgc gat ctg gga ggc aga gac ctg       2112
Ala Val Thr Ala Pro Val Ser Ser Cys Asp Leu Gly Gly Arg Asp Leu
                690                 695                 700 tgc ggt ggc tgc acg ggc agc tcc tca gcc tgc tat gcc ttg gcc acg       2160
Cys Gly Gly Cys Thr Gly Ser Ser Ser Ala Cys Tyr Ala Leu Ala Thr
705                 710                 715                 720 gac ctc cct ggg ggc ctg gaa gca gtg gag gcc cag gag gtt gat gtg       2208
Asp Leu Pro Gly Gly Leu Glu Ala Val Glu Ala Gln Glu Val Asp Val
                725                 730                 735 aat tcg ttt tcc tgg aac ctc aag gaa ctc ttt ttc agt gac cag aca       2256
Asn Ser Phe Ser Trp Asn Leu Lys Glu Leu Phe Phe Ser Asp Gln Thr
                740                 745                 750 gac caa acg tca tca aat tgt tcc tgt gct acg tct gaa ctc aga gag       2304
Asp Gln Thr Ser Ser Asn Cys Ser Cys Ala Thr Ser Glu Leu Arg Glu
            755                 760                 765 aca ccc tct tcc ttg gca gtg ggc tcc gat cca gat gta ggc agt ctc       2352
Thr Pro Ser Ser Leu Ala Val Gly Ser Asp Pro Asp Val Gly Ser Leu
            770                 775                 780 cag gaa cag ggg tcg tgt gtc ctg gat gac agg gag ctg tta cta ctg       2400
Gln Glu Gln Gly Ser Cys Val Leu Asp Asp Arg Glu Leu Leu Leu Leu
785                 790                 795                 800 acc ggc acc tgt gtt gac ctt ggc caa ggc cga cgg ttc cgg gag agc       2448
```

```
                                                              -continued

Thr Gly Thr Cys Val Asp Leu Gly Gln Gly Arg Arg Phe Arg Glu Ser
            805                 810                 815 tgt gtg gga cat gat cca aca gaa ccg ctt gag gtt tgt ttg gtg tcc       2496
Cys Val Gly His Asp Pro Thr Glu Pro Leu Glu Val Cys Leu Val Ser
            820                 825                 830 tct gag cat tat gca gca agc gac aga gaa agc ccg gga cac gtt cct       2544
Ser Glu His Tyr Ala Ala Ser Asp Arg Glu Ser Pro Gly His Val Pro
            835                 840                 845 tcc acg ttg gat gct ggc cct gag gac acg tgc cca tca gca gag gag       2592
Ser Thr Leu Asp Ala Gly Pro Glu Asp Thr Cys Pro Ser Ala Glu Glu
    850                 855                 860 cca agg ctg aac gtc cag gtc acc tcc acg ccc gtg atc gtg atg cgc       2640
Pro Arg Leu Asn Val Gln Val Thr Ser Thr Pro Val Ile Val Met Arg
865                 870                 875                 880 ggg gct gct ggc ctg cag cgg gag atc cag gag ggt gcc tac tcc ggg       2688
Gly Ala Ala Gly Leu Gln Arg Glu Ile Gln Glu Gly Ala Tyr Ser Gly
                885                 890                 895 agc tgc cac cat cga gat ggc tta cgg ctg agt ata cag ttt gag gtg       2736
Ser Cys His His Arg Asp Gly Leu Arg Leu Ser Ile Gln Phe Glu Val
            900                 905                 910 agg cgg gtg gag ctc cag ggc ccc aca cct ctg ttc tgc tgc tgg ctg       2784
Arg Arg Val Glu Leu Gln Gly Pro Thr Pro Leu Phe Cys Cys Trp Leu
            915                 920                 925 gtg aaa gac ctc ctc cac agc caa cgc gac tca gcc gcc agg acc cgc       2832
Val Lys Asp Leu Leu His Ser Gln Arg Asp Ser Ala Ala Arg Thr Arg
930                 935                 940 ctg ttc ctt gcc agc ctg ccc ggc tcc acc cac tct acc gct gct gag       2880
Leu Phe Leu Ala Ser Leu Pro Gly Ser Thr His Ser Thr Ala Ala Glu
945                 950                 955                 960 ctc acc gga ccc agc ctg gtg gaa gtg ctc aga gcc aga ccc tgg ttt       2928
Leu Thr Gly Pro Ser Leu Val Glu Val Leu Arg Ala Arg Pro Trp Phe
                965                 970                 975 gag gag ccc ccc aag gct gtg gaa ctg gag ggg ttg gcg gcc tgt gag       2976
Glu Glu Pro Pro Lys Ala Val Glu Leu Glu Gly Leu Ala Ala Cys Glu
            980                 985                 990 ggc gag tac tcc caa aag tac agt  acc atg agc ccg ctg  ggc agt ggg     3024
Gly Glu Tyr Ser Gln Lys Tyr Ser  Thr Met Ser Pro Leu  Gly Ser Gly
            995                 1000                1005 gcc ttc  ggc ttc gtg tgg act  gct gtg gac aaa gaa  aaa aac aag        3069
Ala Phe  Gly Phe Val Trp Thr  Ala Val Asp Lys Glu  Lys Asn Lys
1010                 1015                 1020 gag gtg  gtg gtg aag ttt att  aag aag gag aag gtc  ttg gag gat        3114
Glu Val  Val Val Lys Phe Ile  Lys Lys Glu Lys Val  Leu Glu Asp
1025                 1030                 1035 tgt tgg  att gag gat ccc aaa  ctt ggg aaa gtt act  tta gag atc        3159
Cys Trp  Ile Glu Asp Pro Lys  Leu Gly Lys Val Thr  Leu Glu Ile
1040                 1045                 1050 gca att  cta tcc agg gtg gag  cac gcc aat atc atc  aag gta ttg        3204
Ala Ile  Leu Ser Arg Val Glu  His Ala Asn Ile Ile  Lys Val Leu
1055                 1060                 1065 gat ata  ttt gaa aac caa ggg  ttc ttc cag ctt gtg  atg gag aag        3249
Asp Ile  Phe Glu Asn Gln Gly  Phe Phe Gln Leu Val  Met Glu Lys
1070                 1075                 1080 cac ggc  tcc ggc cta gac ctc  ttc gct ttc atc gac  cgc cac ccc        3294
His Gly  Ser Gly Leu Asp Leu  Phe Ala Phe Ile Asp  Arg His Pro
1085                 1090                 1095 agg ctg  gat gag ccc ctg gcg  agc tac atc ttc cga  caa cta gtg        3339
Arg Leu  Asp Glu Pro Leu Ala  Ser Tyr Ile Phe Arg  Gln Leu Val
1100                 1105                 1110
```

```
tca gca gtg gga tac ctg cgc ttg aag gac atc atc cac cgt gac    3384
Ser Ala Val Gly Tyr Leu Arg Leu Lys Asp Ile Ile His Arg Asp
    1115            1120                1125 atc aag gat gag aac atc gtg atc gct gag gac ttc aca atc aag    3429
Ile Lys Asp Glu Asn Ile Val Ile Ala Glu Asp Phe Thr Ile Lys
1130            1135                1140 ctg ata gac ttt ggc tcg gcc gcc tac ttg gaa agg gga aaa tta    3474
Leu Ile Asp Phe Gly Ser Ala Ala Tyr Leu Glu Arg Gly Lys Leu
    1145            1150                1155 ttt tat act ttt tgt ggg acc atc gag tac tgt gca ccg gaa gtt    3519
Phe Tyr Thr Phe Cys Gly Thr Ile Glu Tyr Cys Ala Pro Glu Val
    1160            1165                1170 ctc atg ggg aat ccc tac aga ggg ccg gag ctg gag atg tgg tct    3564
Leu Met Gly Asn Pro Tyr Arg Gly Pro Glu Leu Glu Met Trp Ser
    1175            1180                1185 ctg gga gtc act ctg tac acg ctg gtc ttt gag gag aac ccc ttc    3609
Leu Gly Val Thr Leu Tyr Thr Leu Val Phe Glu Glu Asn Pro Phe
    1190            1195                1200 tgt gag ctg gag gag acc gtg gag gct gcc ata cac ccg cca tac    3654
Cys Glu Leu Glu Glu Thr Val Glu Ala Ala Ile His Pro Pro Tyr
    1205            1210                1215 ctg gtg tcc aaa gaa ctc atg agc ctt gtg tct ggg ctg ctg cag    3699
Leu Val Ser Lys Glu Leu Met Ser Leu Val Ser Gly Leu Leu Gln
    1220            1225                1230 cca gtc cct gag aga cgc acc acc ttg gag aag ctg gtg aca gac    3744
Pro Val Pro Glu Arg Arg Thr Thr Leu Glu Lys Leu Val Thr Asp
    1235            1240                1245 ccg tgg gta aca cag cct gtg aat ctt gct gac tat aca tgg gaa    3789
Pro Trp Val Thr Gln Pro Val Asn Leu Ala Asp Tyr Thr Trp Glu
    1250            1255                1260 gag gtg tgt cga gta aac aag cca gaa agt gga gtt ctg tcc gct    3834
Glu Val Cys Arg Val Asn Lys Pro Glu Ser Gly Val Leu Ser Ala
    1265            1270                1275 gcg agc ctg gag atg ggg aac agg agc ctg agt gat gtg gcc cag    3879
Ala Ser Leu Glu Met Gly Asn Arg Ser Leu Ser Asp Val Ala Gln
    1280            1285                1290 gct cag gag ctt tgt ggg ggc ccc gtt cca ggc gag gct cct aat    3924
Ala Gln Glu Leu Cys Gly Gly Pro Val Pro Gly Glu Ala Pro Asn
    1295            1300                1305 ggc caa ggc tgt ttg cat ccc ggg gat ccc cgt ctg ctg acc agc    3969
Gly Gln Gly Cys Leu His Pro Gly Asp Pro Arg Leu Leu Thr Ser
    1310            1315                1320 taa                                                            3972

<210> SEQ ID NO 2
<211> LENGTH: 1323
<212> TYPE: PRT
<213> ORGANISM: human

<400> SEQUENCE: 2

Met Glu Asp Gly Gly Leu Thr Ala Phe Glu Glu Asp Gln Arg Cys Leu
1               5                   10                  15

Ser Gln Ser Leu Pro Leu Pro Val Ser Ala Glu Gly Pro Ala Ala Gln
                20                  25                  30

Thr Thr Ala Glu Pro Ser Arg Ser Phe Ser Ser Ala His Arg His Leu
        35                  40                  45

Ser Arg Arg Asn Gly Leu Ser Arg Leu Cys Gln Ser Arg Thr Ala Leu
    50                  55                  60

Ser Glu Asp Arg Trp Ser Ser Tyr Cys Leu Ser Ser Leu Ala Ala Gln
```

-continued

```
 65                  70                  75                  80
Asn Ile Cys Thr Ser Lys Leu His Cys Pro Ala Ala Pro Glu His Thr
                 85                  90                  95
Asp Pro Ser Glu Pro Arg Gly Ser Val Ser Cys Cys Ser Leu Leu Arg
                100                 105                 110
Gly Leu Ser Ser Gly Trp Ser Ser Pro Leu Leu Pro Ala Pro Val Cys
                115                 120                 125
Asn Pro Asn Lys Ala Ile Phe Thr Val Asp Ala Lys Thr Thr Glu Ile
130                 135                 140
Leu Val Ala Asn Asp Lys Ala Cys Gly Leu Leu Gly Tyr Ser Ser Gln
145                 150                 155                 160
Asp Leu Ile Gly Gln Lys Leu Thr Gln Phe Phe Leu Arg Ser Asp Ser
                165                 170                 175
Asp Val Val Glu Ala Leu Ser Glu Glu His Met Glu Ala Asp Gly His
                180                 185                 190
Ala Ala Val Val Phe Gly Thr Val Asp Ile Ile Ser Arg Ser Gly
                195                 200                 205
Glu Lys Ile Pro Val Ser Val Trp Met Lys Arg Met Arg Gln Glu Arg
                210                 215                 220
Arg Leu Cys Cys Val Val Val Leu Glu Pro Val Glu Arg Val Ser Thr
225                 230                 235                 240
Trp Val Ala Phe Gln Ser Asp Gly Thr Val Thr Ser Cys Asp Ser Leu
                245                 250                 255
Phe Ala His Leu His Gly Tyr Val Ser Gly Glu Asp Val Ala Gly Gln
                260                 265                 270
His Ile Thr Asp Leu Ile Pro Ser Val Gln Leu Pro Pro Ser Gly Gln
                275                 280                 285
His Ile Pro Lys Asn Leu Lys Ile Gln Arg Ser Val Gly Arg Ala Arg
                290                 295                 300
Asp Gly Thr Thr Phe Pro Leu Ser Leu Lys Leu Lys Ser Gln Pro Ser
305                 310                 315                 320
Ser Glu Glu Ala Thr Thr Gly Glu Ala Ala Pro Val Ser Gly Tyr Arg
                325                 330                 335
Ala Ser Val Trp Val Phe Cys Thr Ile Ser Gly Leu Ile Thr Leu Leu
                340                 345                 350
Pro Asp Gly Thr Ile His Gly Ile Asn His Ser Phe Ala Leu Thr Leu
                355                 360                 365
Phe Gly Tyr Gly Lys Thr Glu Leu Leu Gly Lys Asn Ile Thr Phe Leu
                370                 375                 380
Ile Pro Gly Phe Tyr Ser Tyr Met Asp Leu Ala Tyr Asn Ser Ser Leu
385                 390                 395                 400
Gln Leu Pro Asp Leu Ala Ser Cys Leu Asp Val Gly Asn Glu Ser Gly
                405                 410                 415
Cys Gly Glu Arg Thr Leu Asp Pro Trp Gln Gly Gln Asp Pro Ala Glu
                420                 425                 430
Gly Gly Gln Asp Pro Arg Ile Asn Val Val Leu Ala Gly Gly His Val
                435                 440                 445
Val Pro Arg Asp Glu Ile Arg Lys Leu Met Glu Ser Gln Asp Ile Phe
                450                 455                 460
Thr Gly Thr Gln Thr Glu Leu Ile Ala Gly Gly Gln Leu Leu Ser Cys
465                 470                 475                 480
Leu Ser Pro Gln Pro Ala Pro Gly Val Asp Asn Val Pro Glu Gly Ser
                485                 490                 495
```

```
Leu Pro Val His Gly Glu Gln Ala Leu Pro Lys Asp Gln Gln Ile Thr
                500                 505                 510
Ala Leu Gly Arg Glu Glu Pro Val Ala Ile Glu Ser Pro Gly Gln Asp
        515                 520                 525
Leu Leu Gly Glu Ser Arg Ser Glu Pro Val Asp Val Lys Pro Phe Ala
    530                 535                 540
Ser Cys Glu Asp Ser Glu Ala Pro Val Pro Ala Glu Asp Gly Gly Ser
545                 550                 555                 560
Asp Ala Gly Met Cys Gly Leu Cys Gln Lys Ala Gln Leu Glu Arg Met
                565                 570                 575
Gly Val Ser Gly Pro Ser Gly Ser Asp Leu Trp Ala Gly Ala Ala Val
        580                 585                 590
Ala Lys Pro Gln Ala Lys Gly Gln Leu Ala Gly Gly Ser Leu Leu Met
    595                 600                 605
His Cys Pro Cys Tyr Gly Ser Glu Trp Gly Leu Trp Trp Arg Ser Gln
610                 615                 620
Asp Leu Ala Pro Ser Pro Ser Gly Met Ala Gly Leu Ser Phe Gly Thr
                630                 635                 640
625
Pro Thr Leu Asp Glu Pro Trp Leu Gly Val Glu Asn Asp Arg Glu Glu
                645                 650                 655
Leu Gln Thr Cys Leu Ile Lys Glu Gln Leu Ser Gln Leu Ser Leu Ala
                660                 665                 670
Gly Ala Leu Asp Val Pro His Ala Glu Leu Val Pro Thr Glu Cys Gln
                675                 680                 685
Ala Val Thr Ala Pro Val Ser Ser Cys Asp Leu Gly Gly Arg Asp Leu
    690                 695                 700
Cys Gly Gly Cys Thr Gly Ser Ser Ser Ala Cys Tyr Ala Leu Ala Thr
705                 710                 715                 720
Asp Leu Pro Gly Gly Leu Glu Ala Val Glu Ala Gln Glu Val Asp Val
                725                 730                 735
Asn Ser Phe Ser Trp Asn Leu Lys Glu Leu Phe Phe Ser Asp Gln Thr
                740                 745                 750
Asp Gln Thr Ser Ser Asn Cys Ser Cys Ala Thr Ser Glu Leu Arg Glu
        755                 760                 765
Thr Pro Ser Ser Leu Ala Val Gly Ser Asp Pro Asp Val Gly Ser Leu
    770                 775                 780
Gln Glu Gln Gly Ser Cys Val Leu Asp Asp Arg Glu Leu Leu Leu Leu
785                 790                 795                 800
Thr Gly Thr Cys Val Asp Leu Gly Gln Gly Arg Arg Phe Arg Glu Ser
                805                 810                 815
Cys Val Gly His Asp Pro Thr Glu Pro Leu Glu Val Cys Leu Val Ser
                820                 825                 830
Ser Glu His Tyr Ala Ala Ser Asp Arg Glu Ser Pro Gly His Val Pro
        835                 840                 845
Ser Thr Leu Asp Ala Gly Pro Glu Asp Thr Cys Pro Ser Ala Glu Glu
    850                 855                 860
Pro Arg Leu Asn Val Gln Val Thr Ser Thr Pro Val Ile Val Met Arg
865                 870                 875                 880
Gly Ala Ala Gly Leu Gln Arg Glu Ile Gln Glu Gly Ala Tyr Ser Gly
                885                 890                 895
Ser Cys His His Arg Asp Gly Leu Arg Leu Ser Ile Gln Phe Glu Val
                900                 905                 910
```

-continued

```
Arg Arg Val Glu Leu Gln Gly Pro Thr Pro Leu Phe Cys Cys Trp Leu
        915                 920                 925

Val Lys Asp Leu Leu His Ser Gln Arg Asp Ser Ala Ala Arg Thr Arg
        930                 935                 940

Leu Phe Leu Ala Ser Leu Pro Gly Ser Thr His Ser Thr Ala Ala Glu
945                 950                 955                 960

Leu Thr Gly Pro Ser Leu Val Val Leu Arg Ala Arg Pro Trp Phe
                965                 970                 975

Glu Glu Pro Pro Lys Ala Val Glu Leu Glu Gly Leu Ala Ala Cys Glu
                980                 985                 990

Gly Glu Tyr Ser Gln Lys Tyr Ser Thr Met Ser Pro Leu Gly Ser Gly
            995                 1000                1005

Ala Phe Gly Phe Val Trp Thr Ala Val Asp Lys Glu Lys Asn Lys
    1010                1015                1020

Glu Val Val Val Lys Phe Ile Lys Lys Glu Lys Val Leu Glu Asp
    1025                1030                1035

Cys Trp Ile Glu Asp Pro Lys Leu Gly Lys Val Thr Leu Glu Ile
    1040                1045                1050

Ala Ile Leu Ser Arg Val Glu His Ala Asn Ile Lys Val Leu
    1055                1060                1065

Asp Ile Phe Glu Asn Gln Gly Phe Phe Gln Leu Val Met Glu Lys
    1070                1075                1080

His Gly Ser Gly Leu Asp Leu Phe Ala Phe Ile Asp Arg His Pro
    1085                1090                1095

Arg Leu Asp Glu Pro Leu Ala Ser Tyr Ile Phe Arg Gln Leu Val
    1100                1105                1110

Ser Ala Val Gly Tyr Leu Arg Leu Lys Asp Ile Ile His Arg Asp
    1115                1120                1125

Ile Lys Asp Glu Asn Ile Val Ile Ala Glu Asp Phe Thr Ile Lys
    1130                1135                1140

Leu Ile Asp Phe Gly Ser Ala Ala Tyr Leu Glu Arg Gly Lys Leu
    1145                1150                1155

Phe Tyr Thr Phe Cys Gly Thr Ile Glu Tyr Cys Ala Pro Glu Val
    1160                1165                1170

Leu Met Gly Asn Pro Tyr Arg Gly Pro Glu Leu Glu Met Trp Ser
    1175                1180                1185

Leu Gly Val Thr Leu Tyr Thr Leu Val Phe Glu Glu Asn Pro Phe
    1190                1195                1200

Cys Glu Leu Glu Glu Thr Val Glu Ala Ala Ile His Pro Pro Tyr
    1205                1210                1215

Leu Val Ser Lys Glu Leu Met Ser Leu Val Ser Gly Leu Leu Gln
    1220                1225                1230

Pro Val Pro Glu Arg Arg Thr Thr Leu Glu Lys Leu Val Thr Asp
    1235                1240                1245

Pro Trp Val Thr Gln Pro Val Asn Leu Ala Asp Tyr Thr Trp Glu
    1250                1255                1260

Glu Val Cys Arg Val Asn Lys Pro Glu Ser Gly Val Leu Ser Ala
    1265                1270                1275

Ala Ser Leu Glu Met Gly Asn Arg Ser Leu Ser Asp Val Ala Gln
    1280                1285                1290

Ala Gln Glu Leu Cys Gly Gly Pro Val Pro Gly Glu Ala Pro Asn
    1295                1300                1305

Gly Gln Gly Cys Leu His Pro Gly Asp Pro Arg Leu Leu Thr Ser
```

-continued

```
              1310              1315              1320
```

<210> SEQ ID NO 3
<211> LENGTH: 3271
<212> TYPE: DNA
<213> ORGANISM: Drosophila melanogaster
<220> FEATURE:
<221> NAME/KEY: CDS
<222> LOCATION: (121)..(3135)

<400> SEQUENCE: 3

| | |
|---|---|
| atgcgccatt caattgattt tctacgagca gagttcccaa tgtttacggt gcgctcattt | 60 |
| ggttgtagct gtaggcctcg agttggaacc gctgggactt ggaaaacata cgacgcttaa | 120 |

| | | | | | | | | | | | | | | | | |
|---|---|---|---|---|---|---|---|---|---|---|---|---|---|---|---|---|
| atg | gag | gat | cag | ggc | gac | gtg | aca | gac | caa | gcc | gct | ggt | aag | ctg | agt | 168 |
| Met | Glu | Asp | Gln | Gly | Asp | Val | Thr | Asp | Gln | Ala | Ala | Gly | Lys | Leu | Ser | |
| 1 | | | | 5 | | | | | 10 | | | | | 15 | | |
| agt | tcg | aat | gcc | cag | tgc | tcc | aga | aac | cga | tgt | gct | aat | gat | gac | ccc | 216 |
| Ser | Ser | Asn | Ala | Gln | Cys | Ser | Arg | Asn | Arg | Cys | Ala | Asn | Asp | Asp | Pro | |
| | | 20 | | | | | 25 | | | | | 30 | | | | |
| att | atg | ggc | agc | cac | agt | cag | agt | cgc | cag | aac | tcg | tcc | ggc | atg | ctg | 264 |
| Ile | Met | Gly | Ser | His | Ser | Gln | Ser | Arg | Gln | Asn | Ser | Ser | Gly | Met | Leu | |
| | 35 | | | | | 40 | | | | | 45 | | | | | |
| aac | atg | atg | gac | gcc | agc | tcc | ttc | agc | atg | ccc | ccc | ccc | aat | ctg | cac | 312 |
| Asn | Met | Met | Asp | Ala | Ser | Ser | Phe | Ser | Met | Pro | Pro | Pro | Asn | Leu | His | |
| | 50 | | | | | 55 | | | | | 60 | | | | | |
| tcc | tca | aag | gtg | atc | aac | ccg | aac | aag | gcg | ata | ttc | aca | atc | gac | gcg | 360 |
| Ser | Ser | Lys | Val | Ile | Asn | Pro | Asn | Lys | Ala | Ile | Phe | Thr | Ile | Asp | Ala | |
| 65 | | | | | 70 | | | | | 75 | | | | | 80 | |
| aac | aca | ggg | caa | att | ttt | ata | gtg | aac | aac | aag | gcc | tgc | cag | ctg | ctg | 408 |
| Asn | Thr | Gly | Gln | Ile | Phe | Ile | Val | Asn | Asn | Lys | Ala | Cys | Gln | Leu | Leu | |
| | | | 85 | | | | | 90 | | | | | 95 | | | |
| ggc | tac | acg | tcg | cag | gag | ttg | agg | aac | aag | gga | ttc | ttc | gac | ctg | ctt | 456 |
| Gly | Tyr | Thr | Ser | Gln | Glu | Leu | Arg | Asn | Lys | Gly | Phe | Phe | Asp | Leu | Leu | |
| | | | | 100 | | | | | 105 | | | | | 110 | | |
| aac | ggc | aag | aca | gag | agc | cac | atc | tcc | tcc | ctg | gcg | gag | atg | cag | atc | 504 |
| Asn | Gly | Lys | Thr | Glu | Ser | His | Ile | Ser | Ser | Leu | Ala | Glu | Met | Gln | Ile | |
| | | 115 | | | | | 120 | | | | | 125 | | | | |
| gaa | ggc | gat | gag | ggc | cgg | gtc | gtc | ctg | cta | agt | gga | aag | gtc | atc | gag | 552 |
| Glu | Gly | Asp | Glu | Gly | Arg | Val | Val | Leu | Leu | Ser | Gly | Lys | Val | Ile | Glu | |
| | 130 | | | | | 135 | | | | | 140 | | | | | |
| atg | aag | acc | aag | tcg | ggc | ggc | aag | atc | ctg | gtc | tct | ctc | tgg | atc | cgg | 600 |
| Met | Lys | Thr | Lys | Ser | Gly | Gly | Lys | Ile | Leu | Val | Ser | Leu | Trp | Ile | Arg | |
| 145 | | | | | 150 | | | | | 155 | | | | | 160 | |
| cag | atc | agc | agc | gat | ggc | cga | cac | ata | gcc | gtc | gcg | gag | cct | gtg | gag | 648 |
| Gln | Ile | Ser | Ser | Asp | Gly | Arg | His | Ile | Ala | Val | Ala | Glu | Pro | Val | Glu | |
| | | | | 165 | | | | | 170 | | | | | 175 | | |
| agg | cat | att | tgc | cac | atc | agc | acc | gat | aga | tcc | gga | gtg | ata | aca | tcc | 696 |
| Arg | His | Ile | Cys | His | Ile | Ser | Thr | Asp | Arg | Ser | Gly | Val | Ile | Thr | Ser | |
| | | | 180 | | | | | 185 | | | | | 190 | | | |
| gtt | gac | tcc | acc | acg | gcc | acc | ata | ttc | ttt | tat | gaa | tcc | gtc | gaa | agc | 744 |
| Val | Asp | Ser | Thr | Thr | Ala | Thr | Ile | Phe | Phe | Tyr | Glu | Ser | Val | Glu | Ser | |
| | | 195 | | | | | 200 | | | | | 205 | | | | |
| gtg | gtg | ggt | gtc | agc | att | gtc | acc | ctt | atc | ccg | ttt | ata | aag | ctg | ccc | 792 |
| Val | Val | Gly | Val | Ser | Ile | Val | Thr | Leu | Ile | Pro | Phe | Ile | Lys | Leu | Pro | |
| | 210 | | | | | 215 | | | | | 220 | | | | | |
| gat | ccg | gat | agc | cgt | gag | atc | ccc | aag | agc | ctg | cgg | aag | cag | aga | gct | 840 |
| Asp | Pro | Asp | Ser | Arg | Glu | Ile | Pro | Lys | Ser | Leu | Arg | Lys | Gln | Arg | Ala | |
| 225 | | | | | 230 | | | | | 235 | | | | | 240 | |
| act | ggt | cga | act | acg | gat | aac | gta | aag | ttt | ccc | ctg | tgc | ttg | cta | ata | 888 |
| Thr | Gly | Arg | Thr | Thr | Asp | Asn | Val | Lys | Phe | Pro | Leu | Cys | Leu | Leu | Ile | |

-continued

|     |     |     |     | 245 |     |     |     | 250 |     |     |     | 255 |     |     |      |
| gcc | ctg | gac | gag | gat | gct | tct | gcg | ggg | tat | tcc | cat | tcg | gga | aaa | acc  | 936 |
| Ala | Leu | Asp | Glu | Asp | Ala | Ser | Ala | Gly | Tyr | Ser | His | Ser | Gly | Lys | Thr  |
|     |     |     |     | 260 |     |     |     | 265 |     |     |     | 270 |     |     |      |

| ggt | cta | aat | atc | acc | gtc | tgg | gtg | ttc | cag | aat | ctt | agt | ggc | ctg | att | 984 |
| Gly | Leu | Asn | Ile | Thr | Val | Trp | Val | Phe | Gln | Asn | Leu | Ser | Gly | Leu | Ile |
|     |     |     | 275 |     |     |     | 280 |     |     |     | 285 |     |     |     |     |

| gtg | gta | gat | gac | ata | ggc | aac | ata | ctg | atg | tgc | aac | cag | cct | ttc | tcg | 1032 |
| Val | Val | Asp | Asp | Ile | Gly | Asn | Ile | Leu | Met | Cys | Asn | Gln | Pro | Phe | Ser |
|     |     | 290 |     |     |     | 295 |     |     |     | 300 |     |     |     |     |     |

| ctg | cta | atg | ttc | gga | tat | ggt | cag | gac | aag | ata | atg | aac | atg | cat | ata | 1080 |
| Leu | Leu | Met | Phe | Gly | Tyr | Gly | Gln | Asp | Lys | Ile | Met | Asn | Met | His | Ile |
| 305 |     |     |     | 310 |     |     |     | 315 |     |     |     | 320 |     |     |     |

| tcg | gcg | atc | cta | ccc | aat | ttc | ggc | aag | gac | tct | cgc | gag | gag | aag | agt | 1128 |
| Ser | Ala | Ile | Leu | Pro | Asn | Phe | Gly | Lys | Asp | Ser | Arg | Glu | Glu | Lys | Ser |
|     |     |     |     | 325 |     |     |     | 330 |     |     |     | 335 |     |     |     |

| ccg | aat | gtt | tcg | aac | acc | tcg | ata | acc | agt | aac | gac | tgg | gag | ccg | gac | 1176 |
| Pro | Asn | Val | Ser | Asn | Thr | Ser | Ile | Thr | Ser | Asn | Asp | Trp | Glu | Pro | Asp |
|     |     |     |     | 340 |     |     |     | 345 |     |     |     | 350 |     |     |     |

| acg | gat | ccc | ctc | gtc | gtg | gac | aac | gac | tcc | tcg | ctg | caa | tcc | tgc | aag | 1224 |
| Thr | Asp | Pro | Leu | Val | Val | Asp | Asn | Asp | Ser | Ser | Leu | Gln | Ser | Cys | Lys |
|     |     |     | 355 |     |     |     | 360 |     |     |     | 365 |     |     |     |     |

| aag | agc | tcg | act | aac | agg | acg | gcg | ccc | aac | aac | gaa | cag | tct | tcg | gtg | 1272 |
| Lys | Ser | Ser | Thr | Asn | Arg | Thr | Ala | Pro | Asn | Asn | Glu | Gln | Ser | Ser | Val |
|     | 370 |     |     |     | 375 |     |     |     | 380 |     |     |     |     |     |     |

| ggc | gat | gcc | cac | cta | agc | tgc | aat | ctg | gag | aac | agc | agt | ggt | cta | ttc | 1320 |
| Gly | Asp | Ala | His | Leu | Ser | Cys | Asn | Leu | Glu | Asn | Ser | Ser | Gly | Leu | Phe |
| 385 |     |     |     | 390 |     |     |     | 395 |     |     |     |     |     |     | 400 |

| tgc | gac | ctc | cgc | cag | cca | gat | gat | tgt | aca | ata | gat | gac | att | cta | aca | 1368 |
| Cys | Asp | Leu | Arg | Gln | Pro | Asp | Asp | Cys | Thr | Ile | Asp | Asp | Ile | Leu | Thr |
|     |     |     |     | 405 |     |     |     | 410 |     |     |     | 415 |     |     |     |

| cct | gta | aat | gcc | tca | aac | agt | ttc | ccc | gct | gac | gag | ttt | gag | gta | gga | 1416 |
| Pro | Val | Asn | Ala | Ser | Asn | Ser | Phe | Pro | Ala | Asp | Glu | Phe | Glu | Val | Gly |
|     |     |     | 420 |     |     |     | 425 |     |     |     | 430 |     |     |     |     |

| tcg | cag | tcg | cag | gtg | aat | gag | tcg | tcc | ctt | gac | aag | gcg | aag | tcc | gcg | 1464 |
| Ser | Gln | Ser | Gln | Val | Asn | Glu | Ser | Ser | Leu | Asp | Lys | Ala | Lys | Ser | Ala |
|     |     | 435 |     |     |     | 440 |     |     |     | 445 |     |     |     |     |     |

| tcc | acg | gag | acc | tgt | gat | gcc | tcc | ggc | agc | aat | ccc | gcc | acc | aga | ctg | 1512 |
| Ser | Thr | Glu | Thr | Cys | Asp | Ala | Ser | Gly | Ser | Asn | Pro | Ala | Thr | Arg | Leu |
|     | 450 |     |     |     | 455 |     |     |     | 460 |     |     |     |     |     |     |

| ctt | agt | tcc | atc | aac | gga | agc | ttt | gtg | ggg | gag | gcc | att | cac | gcc | gat | 1560 |
| Leu | Ser | Ser | Ile | Asn | Gly | Ser | Phe | Val | Gly | Glu | Ala | Ile | His | Ala | Asp |
| 465 |     |     |     | 470 |     |     |     | 475 |     |     |     | 480 |     |     |     |

| ggc | tcc | gtc | ata | gag | gta | gtc | tac | tcc | gtg | ctc | ctc | cag | ata | ctg | ccc | 1608 |
| Gly | Ser | Val | Ile | Glu | Val | Val | Tyr | Ser | Val | Leu | Leu | Gln | Ile | Leu | Pro |
|     |     |     |     | 485 |     |     |     | 490 |     |     |     | 495 |     |     |     |

| tgc | tcc | aac | cgg | gtg | tac | tgc | atc | tgg | gtg | tgc | cgc | aac | ccc | agc | act | 1656 |
| Cys | Ser | Asn | Arg | Val | Tyr | Cys | Ile | Trp | Val | Cys | Arg | Asn | Pro | Ser | Thr |
|     |     |     | 500 |     |     |     | 505 |     |     |     | 510 |     |     |     |     |

| cgg | ctg | gac | ggt | gag | aag | tac | aac | tat | gca | aac | cta | acg | tcc | aca | ttc | 1704 |
| Arg | Leu | Asp | Gly | Glu | Lys | Tyr | Asn | Tyr | Ala | Asn | Leu | Thr | Ser | Thr | Phe |
|     |     | 515 |     |     |     | 520 |     |     |     | 525 |     |     |     |     |     |

| aac | agc | atg | gcc | agc | act | gtt | gag | cag | tcg | ctg | ggc | cag | gtg | ata | aag | 1752 |
| Asn | Ser | Met | Ala | Ser | Thr | Val | Glu | Gln | Ser | Leu | Gly | Gln | Val | Ile | Lys |
|     | 530 |     |     |     | 535 |     |     |     | 540 |     |     |     |     |     |     |

| acc | acc | gct | gcc | cag | aac | tcc | agc | aga | ccc | aat | tct | ctg | tcc | ttg | gtg | 1800 |
| Thr | Thr | Ala | Ala | Gln | Asn | Ser | Ser | Arg | Pro | Asn | Ser | Leu | Ser | Leu | Val |
| 545 |     |     |     | 550 |     |     |     | 555 |     |     |     | 560 |     |     |     |

| tcc | aag | tac | gag | gac | gaa | ttg | tac | ctg | ggc | gac | tac | agc | aaa | tac | tac | 1848 |

```
Ser Lys Tyr Glu Asp Glu Leu Tyr Leu Gly Asp Tyr Ser Lys Tyr Tyr
            565                 570                 575 acg tcc atc cgc cag atc gga aga gga gcc tat ggg tat gtg aat atg    1896
Thr Ser Ile Arg Gln Ile Gly Arg Gly Ala Tyr Gly Tyr Val Asn Met
            580                 585                 590 gct ttc cgg aac agc gac cgc ctg ctg gtg atc acc aag ttt att ctc    1944
Ala Phe Arg Asn Ser Asp Arg Leu Leu Val Ile Thr Lys Phe Ile Leu
            595                 600                 605 aag gag aag ctc tgc tct cag ttt atg gtt aag agc cgc gac tgc aag    1992
Lys Glu Lys Leu Cys Ser Gln Phe Met Val Lys Ser Arg Asp Cys Lys
            610                 615                 620 gaa gtt cct atc gag atc cac ctg ctg cag acc ctg aac cac aag aac    2040
Glu Val Pro Ile Glu Ile His Leu Leu Gln Thr Leu Asn His Lys Asn
625                 630                 635                 640 att gtg tcc gtt ctc gat gtt ttc gaa aat gat cta ttc tac cag ctg    2088
Ile Val Ser Val Leu Asp Val Phe Glu Asn Asp Leu Phe Tyr Gln Leu
            645                 650                 655 gtc atg gag aag cac gga tcc gga atg gat cta tgg acg ttc ata gag    2136
Val Met Glu Lys His Gly Ser Gly Met Asp Leu Trp Thr Phe Ile Glu
            660                 665                 670 cgg cgg ccc ctg atg gac gaa aag ctg gga agc tac att ttt cgt cag    2184
Arg Arg Pro Leu Met Asp Glu Lys Leu Gly Ser Tyr Ile Phe Arg Gln
            675                 680                 685 gtg gcc gat gcc gtc aac tat ctg cac gaa cag aag ata ctg cat cgg    2232
Val Ala Asp Ala Val Asn Tyr Leu His Glu Gln Lys Ile Leu His Arg
            690                 695                 700 gac atc aag gac gag aac att ata att gac cag aac ttc acc ata aag    2280
Asp Ile Lys Asp Glu Asn Ile Ile Ile Asp Gln Asn Phe Thr Ile Lys
705                 710                 715                 720 ctg att gac ttc gga tcg gcg acc ttc atg gag gag gga aaa ttc ttc    2328
Leu Ile Asp Phe Gly Ser Ala Thr Phe Met Glu Glu Gly Lys Phe Phe
            725                 730                 735 tcc acg ttc tac ggc acg acg gag tac tgc agt ccg gag gtt ctg gcc    2376
Ser Thr Phe Tyr Gly Thr Thr Glu Tyr Cys Ser Pro Glu Val Leu Ala
            740                 745                 750 gga aac aga tac gtg ggt ccc gag ctg gag att tgg gcc ctt ggt gtg    2424
Gly Asn Arg Tyr Val Gly Pro Glu Leu Glu Ile Trp Ala Leu Gly Val
            755                 760                 765 acg ctt tac gtt ctg atg ttt ttc gaa aat cca ttc atc gat gtg gag    2472
Thr Leu Tyr Val Leu Met Phe Phe Glu Asn Pro Phe Ile Asp Val Glu
770                 775                 780 gag aca ttg aag gcc gag att caa ata ccg aaa gct gtg tcc gag caa    2520
Glu Thr Leu Lys Ala Glu Ile Gln Ile Pro Lys Ala Val Ser Glu Gln
785                 790                 795                 800 ttg agc cgt ctg ttg agc tcc atg ctg aat aag gat ccc aag tac cgg    2568
Leu Ser Arg Leu Leu Ser Ser Met Leu Asn Lys Asp Pro Lys Tyr Arg
            805                 810                 815 tgc acc atg cac cag tta atc aca gat cca tgg ctc acc cag gag gtg    2616
Cys Thr Met His Gln Leu Ile Thr Asp Pro Trp Leu Thr Gln Glu Val
            820                 825                 830 aat ccc tct act ttc agt ttc tcg tgg ata gtg ccg tgc aag gcc cac    2664
Asn Pro Ser Thr Phe Ser Phe Ser Trp Ile Val Pro Cys Lys Ala His
            835                 840                 845 gag gcc aat ccg aat ctg tat ttt tcc ggc tac cta tac tcc agt act    2712
Glu Ala Asn Pro Asn Leu Tyr Phe Ser Gly Tyr Leu Tyr Ser Ser Thr
            850                 855                 860 tcg gtg ctg tcc act att tca ccg cag gag agc ttc tcc cac atc gag    2760
Ser Val Leu Ser Thr Ile Ser Pro Gln Glu Ser Phe Ser His Ile Glu
865                 870                 875                 880
```

```
gag tcc tcg att ggg ggc agc gat gac gcc aga tta gca tcc cac aga    2808
Glu Ser Ser Ile Gly Gly Ser Asp Asp Ala Arg Leu Ala Ser His Arg
                885                 890                 895 acc gga cac aag ttg tgc gtt aat gaa ggt aca ata ctt ctt cgt ctg    2856
Thr Gly His Lys Leu Cys Val Asn Glu Gly Thr Ile Leu Leu Arg Leu
            900                 905                 910 ctg cgt att tta gtt gta aag cat ccc ttt gtc att cta gcc aag cac    2904
Leu Arg Ile Leu Val Val Lys His Pro Phe Val Ile Leu Ala Lys His
        915                 920                 925 aac aaa atg gac act ctt tac gcg aaa cag ttc cag cta aac acc tca    2952
Asn Lys Met Asp Thr Leu Tyr Ala Lys Gln Phe Gln Leu Asn Thr Ser
    930                 935                 940 gtg agt aac cac gag ctg agg gtc tcg tta cct gac tca agc cac aca    3000
Val Ser Asn His Glu Leu Arg Val Ser Leu Pro Asp Ser Ser His Thr
945                 950                 955                 960 gaa atc ggc ggt tca ata tgc tcc tcg aaa tcc gag aac gat ata ttc    3048
Glu Ile Gly Gly Ser Ile Cys Ser Ser Lys Ser Glu Asn Asp Ile Phe
                965                 970                 975 aag aac aag ctt cag ccc tgc gtc tcc act tat aac gta gtt agt ctg    3096
Lys Asn Lys Leu Gln Pro Cys Val Ser Thr Tyr Asn Val Val Ser Leu
            980                 985                 990 cac gac gtg agc acg aaa ccc aag  aag ctt gat ctg aaa   tgaagttcga  3145
His Asp Val Ser Thr Lys Pro Lys  Lys Leu Asp Leu Lys
        995                 1000              1005 aatccgttgt gtacatgtgt aaatcgaatc tgagcatact gtcatatgta aatagcaaca   3205
tttgtgaaag gacaattaag tattggggcg gaaaagcatg tagatgaata aatcaattta   3265
attgtt                                                              3271

<210> SEQ ID NO 4
<211> LENGTH: 1005
<212> TYPE: PRT
<213> ORGANISM: Drosophila melanogaster

<400> SEQUENCE: 4

Met Glu Asp Gln Gly Asp Val Thr Asp Gln Ala Ala Gly Lys Leu Ser
1               5                   10                  15

Ser Ser Asn Ala Gln Cys Ser Arg Asn Arg Cys Ala Asn Asp Asp Pro
            20                  25                  30

Ile Met Gly Ser His Ser Gln Ser Arg Gln Asn Ser Ser Gly Met Leu
        35                  40                  45

Asn Met Met Asp Ala Ser Ser Phe Ser Met Pro Pro Asn Leu His
    50                  55                  60

Ser Ser Lys Val Ile Asn Pro Asn Lys Ala Ile Phe Thr Ile Asp Ala
65                  70                  75                  80

Asn Thr Gly Gln Ile Phe Ile Val Asn Lys Ala Cys Gln Leu Leu
                85                  90                  95

Gly Tyr Thr Ser Gln Glu Leu Arg Asn Lys Gly Phe Phe Asp Leu Leu
            100                 105                 110

Asn Gly Lys Thr Glu Ser His Ile Ser Ser Leu Ala Glu Met Gln Ile
        115                 120                 125

Glu Gly Asp Glu Gly Arg Val Val Leu Leu Ser Gly Lys Val Ile Glu
    130                 135                 140

Met Lys Thr Lys Ser Gly Gly Lys Ile Leu Val Ser Leu Trp Ile Arg
145                 150                 155                 160

Gln Ile Ser Ser Asp Gly Arg His Ile Ala Val Ala Glu Pro Val Glu
                165                 170                 175
```

-continued

```
Arg His Ile Cys His Ile Ser Thr Asp Arg Ser Gly Val Ile Thr Ser
                180                 185                 190
Val Asp Ser Thr Thr Ala Thr Ile Phe Phe Tyr Glu Ser Val Glu Ser
            195                 200                 205
Val Val Gly Val Ser Ile Val Thr Leu Ile Pro Phe Ile Lys Leu Pro
        210                 215                 220
Asp Pro Asp Ser Arg Glu Ile Pro Lys Ser Leu Arg Lys Gln Arg Ala
225                 230                 235                 240
Thr Gly Arg Thr Thr Asp Asn Val Lys Phe Pro Leu Cys Leu Leu Ile
                245                 250                 255
Ala Leu Asp Glu Asp Ala Ser Ala Gly Tyr Ser His Ser Gly Lys Thr
            260                 265                 270
Gly Leu Asn Ile Thr Val Trp Val Phe Gln Asn Leu Ser Gly Leu Ile
        275                 280                 285
Val Val Asp Asp Ile Gly Asn Ile Leu Met Cys Asn Gln Pro Phe Ser
    290                 295                 300
Leu Leu Met Phe Gly Tyr Gly Gln Asp Lys Ile Met Asn Met His Ile
305                 310                 315                 320
Ser Ala Ile Leu Pro Asn Phe Gly Lys Asp Ser Arg Glu Glu Lys Ser
                325                 330                 335
Pro Asn Val Ser Asn Thr Ser Ile Thr Ser Asn Asp Trp Glu Pro Asp
            340                 345                 350
Thr Asp Pro Leu Val Val Asp Asn Asp Ser Ser Leu Gln Ser Cys Lys
        355                 360                 365
Lys Ser Ser Thr Asn Arg Thr Ala Pro Asn Asn Glu Gln Ser Ser Val
370                 375                 380
Gly Asp Ala His Leu Ser Cys Asn Leu Glu Asn Ser Ser Gly Leu Phe
385                 390                 395                 400
Cys Asp Leu Arg Gln Pro Asp Asp Cys Thr Ile Asp Asp Ile Leu Thr
                405                 410                 415
Pro Val Asn Ala Ser Asn Ser Phe Pro Ala Asp Glu Phe Glu Val Gly
            420                 425                 430
Ser Gln Ser Gln Val Asn Glu Ser Ser Leu Asp Lys Ala Lys Ser Ala
        435                 440                 445
Ser Thr Glu Thr Cys Asp Ala Ser Gly Ser Asn Pro Ala Thr Arg Leu
    450                 455                 460
Leu Ser Ser Ile Asn Gly Ser Phe Val Gly Glu Ala Ile His Ala Asp
465                 470                 475                 480
Gly Ser Val Ile Glu Val Val Tyr Ser Val Leu Leu Gln Ile Leu Pro
                485                 490                 495
Cys Ser Asn Arg Val Tyr Cys Ile Trp Val Cys Arg Asn Pro Ser Thr
            500                 505                 510
Arg Leu Asp Gly Glu Lys Tyr Asn Tyr Ala Asn Leu Thr Ser Thr Phe
        515                 520                 525
Asn Ser Met Ala Ser Thr Val Glu Gln Ser Leu Gly Gln Val Ile Lys
    530                 535                 540
Thr Thr Ala Ala Gln Asn Ser Ser Arg Pro Asn Ser Leu Ser Leu Val
545                 550                 555                 560
Ser Lys Tyr Glu Asp Glu Leu Tyr Leu Gly Asp Tyr Ser Lys Tyr Tyr
                565                 570                 575
Thr Ser Ile Arg Gln Ile Gly Arg Gly Ala Tyr Gly Tyr Val Asn Met
            580                 585                 590
Ala Phe Arg Asn Ser Asp Arg Leu Leu Val Ile Thr Lys Phe Ile Leu
```

595                 600                 605
Lys Glu Lys Leu Cys Ser Gln Phe Met Val Lys Ser Arg Asp Cys Lys
    610                 615                 620

Glu Val Pro Ile Glu Ile His Leu Leu Gln Thr Leu Asn His Lys Asn
625                 630                 635                 640

Ile Val Ser Val Leu Asp Val Phe Glu Asn Asp Leu Phe Tyr Gln Leu
                645                 650                 655

Val Met Glu Lys His Gly Ser Gly Met Asp Leu Trp Thr Phe Ile Glu
            660                 665                 670

Arg Arg Pro Leu Met Asp Glu Lys Leu Gly Ser Tyr Ile Phe Arg Gln
        675                 680                 685

Val Ala Asp Ala Val Asn Tyr Leu His Glu Gln Lys Ile Leu His Arg
    690                 695                 700

Asp Ile Lys Asp Glu Asn Ile Ile Asp Gln Asn Phe Thr Ile Lys
705                 710                 715                 720

Leu Ile Asp Phe Gly Ser Ala Thr Phe Met Glu Gly Lys Phe Phe
                725                 730                 735

Ser Thr Phe Tyr Gly Thr Thr Glu Tyr Cys Ser Pro Glu Val Leu Ala
            740                 745                 750

Gly Asn Arg Tyr Val Gly Pro Glu Leu Glu Ile Trp Ala Leu Gly Val
        755                 760                 765

Thr Leu Tyr Val Leu Met Phe Phe Glu Asn Pro Phe Ile Asp Val Glu
    770                 775                 780

Glu Thr Leu Lys Ala Glu Ile Gln Ile Pro Lys Ala Val Ser Glu Gln
785                 790                 795                 800

Leu Ser Arg Leu Leu Ser Ser Met Leu Asn Lys Asp Pro Lys Tyr Arg
                805                 810                 815

Cys Thr Met His Gln Leu Ile Thr Asp Pro Trp Leu Thr Gln Glu Val
            820                 825                 830

Asn Pro Ser Thr Phe Ser Phe Ser Trp Ile Val Pro Cys Lys Ala His
        835                 840                 845

Glu Ala Asn Pro Asn Leu Tyr Phe Ser Gly Tyr Leu Tyr Ser Ser Thr
    850                 855                 860

Ser Val Leu Ser Thr Ile Ser Pro Gln Glu Ser Phe Ser His Ile Glu
865                 870                 875                 880

Glu Ser Ser Ile Gly Gly Ser Asp Asp Ala Arg Leu Ala Ser His Arg
                885                 890                 895

Thr Gly His Lys Leu Cys Val Asn Glu Gly Thr Ile Leu Leu Arg Leu
            900                 905                 910

Leu Arg Ile Leu Val Val Lys His Pro Phe Val Ile Leu Ala Lys His
        915                 920                 925

Asn Lys Met Asp Thr Leu Tyr Ala Lys Gln Phe Gln Leu Asn Thr Ser
    930                 935                 940

Val Ser Asn His Glu Leu Arg Val Ser Leu Pro Asp Ser Ser His Thr
945                 950                 955                 960

Glu Ile Gly Gly Ser Ile Cys Ser Ser Lys Ser Glu Asn Asp Ile Phe
                965                 970                 975

Lys Asn Lys Leu Gln Pro Cys Val Ser Thr Tyr Asn Val Ser Leu
            980                 985                 990

His Asp Val Ser Thr Lys Pro Lys Lys Leu Asp Leu Lys
            995                1000                1005

<210> SEQ ID NO 5

```
<211> LENGTH: 4071
<212> TYPE: DNA
<213> ORGANISM: yeast
<220> FEATURE:
<221> NAME/KEY: CDS
<222> LOCATION: (1)..(4068)

<400> SEQUENCE: 5 atg ccc tac atc ggt gct tcc aac ctc tca gaa cat tca ttt gtt aat      48
Met Pro Tyr Ile Gly Ala Ser Asn Leu Ser Glu His Ser Phe Val Asn
1               5                   10                  15 ttg aag gaa aaa cat gcg att aca cat aaa ggt acg agc agt tct gta      96
Leu Lys Glu Lys His Ala Ile Thr His Lys Gly Thr Ser Ser Ser Val
            20                  25                  30 gca tct ttg cag aca cca ccg agc ccc gat caa gag aac cat att gac     144
Ala Ser Leu Gln Thr Pro Pro Ser Pro Asp Gln Glu Asn His Ile Asp
        35                  40                  45 aat gaa tta gaa aat tac gat acg tct tta agt gac gtt tca acc ccg     192
Asn Glu Leu Glu Asn Tyr Asp Thr Ser Leu Ser Asp Val Ser Thr Pro
    50                  55                  60 aat aaa aag gaa ggt gat gag ttc cag caa agt tta aga gat aca ttt     240
Asn Lys Lys Glu Gly Asp Glu Phe Gln Gln Ser Leu Arg Asp Thr Phe
65                  70                  75                  80 gcg agc ttt cgg aag act aaa ccc cca cct cct tta gat ttt gaa caa     288
Ala Ser Phe Arg Lys Thr Lys Pro Pro Pro Pro Leu Asp Phe Glu Gln
                85                  90                  95 cca aga ctt cct tcg aca gct tct tca tcc gtt gat tca acc gta tca     336
Pro Arg Leu Pro Ser Thr Ala Ser Ser Ser Val Asp Ser Thr Val Ser
            100                 105                 110 tcg ccc tta acg gat gaa gac ata aag gag tta gag ttt ctt ccg aat     384
Ser Pro Leu Thr Asp Glu Asp Ile Lys Glu Leu Glu Phe Leu Pro Asn
        115                 120                 125 gaa tca act cat tct tat tcg tac aat cca ctt tcg cca aat tcc ctg     432
Glu Ser Thr His Ser Tyr Ser Tyr Asn Pro Leu Ser Pro Asn Ser Leu
    130                 135                 140 gca gtc aga ttg agg att ttg aag aga tca ttg gaa atc ata ata caa     480
Ala Val Arg Leu Arg Ile Leu Lys Arg Ser Leu Glu Ile Ile Ile Gln
145                 150                 155                 160 aac cca agt atg cta ctg gag cct act cca gat gat ttg cct cct ttg     528
Asn Pro Ser Met Leu Leu Glu Pro Thr Pro Asp Asp Leu Pro Pro Leu
                165                 170                 175 aaa gag ttt gcg ggc cgt agg agc agt tta cca agg aca tcg gct tct     576
Lys Glu Phe Ala Gly Arg Arg Ser Ser Leu Pro Arg Thr Ser Ala Ser
            180                 185                 190 gca aac cat tta atg aac aga aat aag agc cag att tgg aac act act     624
Ala Asn His Leu Met Asn Arg Asn Lys Ser Gln Ile Trp Asn Thr Thr
        195                 200                 205 tcc gct act tta aat gca ttt gta aat aat acc tct tcc tcc tca gca     672
Ser Ala Thr Leu Asn Ala Phe Val Asn Asn Thr Ser Ser Ser Ser Ala
    210                 215                 220 gca tct tct gct tta tct aac aaa aaa ccg ggc acc cca gtt ttc cct     720
Ala Ser Ser Ala Leu Ser Asn Lys Lys Pro Gly Thr Pro Val Phe Pro
225                 230                 235                 240 aat ttg gat cca aca cat tct caa aca ttc cat aga gcc aac tcg ttg     768
Asn Leu Asp Pro Thr His Ser Gln Thr Phe His Arg Ala Asn Ser Leu
                245                 250                 255 gct tat tta cct tcc atc tta cct gag caa gat ccg ctg ctc aaa cat     816
Ala Tyr Leu Pro Ser Ile Leu Pro Glu Gln Asp Pro Leu Leu Lys His
            260                 265                 270 aat aat tct tta ttt cgt ggc gac tat gga aac aac ata agt cct gaa     864
Asn Asn Ser Leu Phe Arg Gly Asp Tyr Gly Asn Asn Ile Ser Pro Glu
```

-continued

|     | 275 |     |     |     | 280 |     |     |     | 285 |     |     |      |
|-----|-----|-----|-----|-----|-----|-----|-----|-----|-----|-----|-----|------|
| agg | cca | agt | ttt | aga | caa | ccc | ttc | aag | gat | caa | act | agc aat ctc cgc | 912 |
| Arg | Pro | Ser | Phe | Arg | Gln | Pro | Phe | Lys | Asp | Gln | Thr | Ser Asn Leu Arg |     |
|     | 290 |     |     |     | 295 |     |     |     | 300 |     |     |      |

```
agg cca agt ttt aga caa ccc ttc aag gat caa act agc aat ctc cgc       912
Arg Pro Ser Phe Arg Gln Pro Phe Lys Asp Gln Thr Ser Asn Leu Arg
    290                 295                 300 aat agc agt tta ctc aat gag agg gca tat cag gaa gat gaa act ttt       960
Asn Ser Ser Leu Leu Asn Glu Arg Ala Tyr Gln Glu Asp Glu Thr Phe
305                 310                 315                 320 tta ccg cac cat gga ccc tct atg gat cta ttg aat gaa caa aga gcg      1008
Leu Pro His His Gly Pro Ser Met Asp Leu Leu Asn Glu Gln Arg Ala
                325                 330                 335 aac ttg aaa agt ctt ctg aat tta tta aac gaa aca ctg gag aaa aat      1056
Asn Leu Lys Ser Leu Leu Asn Leu Leu Asn Glu Thr Leu Glu Lys Asn
                340                 345                 350 act tcc gag aga gct tcg gat ctt cat atg ata tcg ttg ttc aat ttg      1104
Thr Ser Glu Arg Ala Ser Asp Leu His Met Ile Ser Leu Phe Asn Leu
            355                 360                 365 aat aaa cta atg ctt gga gat ccc aag aaa aat aat tca gaa cgc gat      1152
Asn Lys Leu Met Leu Gly Asp Pro Lys Lys Asn Asn Ser Glu Arg Asp
370                 375                 380 aaa aga act gaa aag ctt aaa aag att ttg ctg gat agt ctt gca gaa      1200
Lys Arg Thr Glu Lys Leu Lys Lys Ile Leu Leu Asp Ser Leu Ala Glu
385                 390                 395                 400 cca ttc ttt gag cac tat aat ttt att gga gat aat ccg atc gca gat      1248
Pro Phe Phe Glu His Tyr Asn Phe Ile Gly Asp Asn Pro Ile Ala Asp
                405                 410                 415 aca gat gaa cta aag gag gaa att gat gaa ttt aca ggt tct gga gat      1296
Thr Asp Glu Leu Lys Glu Glu Ile Asp Glu Phe Thr Gly Ser Gly Asp
            420                 425                 430 acg aca gcg ata aca gat ata cgg ccc caa cag gac tat ggc cgc ata      1344
Thr Thr Ala Ile Thr Asp Ile Arg Pro Gln Gln Asp Tyr Gly Arg Ile
            435                 440                 445 ttg agg aca ttc act tct acc aaa aat tcc gcc cca cag gca att ttt      1392
Leu Arg Thr Phe Thr Ser Thr Lys Asn Ser Ala Pro Gln Ala Ile Phe
    450                 455                 460 aca tgt agt cag gaa gac cct tgg caa ttc aga gct gcg aat gat cta      1440
Thr Cys Ser Gln Glu Asp Pro Trp Gln Phe Arg Ala Ala Asn Asp Leu
465                 470                 475                 480 gcg tgc tta gta ttc ggt atc tca cag aat gcc att cgc gct tta acc      1488
Ala Cys Leu Val Phe Gly Ile Ser Gln Asn Ala Ile Arg Ala Leu Thr
                485                 490                 495 ttg atg gat tta att cac acc gat agc aga aat ttt gtt tta cac aaa      1536
Leu Met Asp Leu Ile His Thr Asp Ser Arg Asn Phe Val Leu His Lys
            500                 505                 510 tta ctt tct acg gag ggt caa gaa atg gtt ttc aca ggc gaa atc att      1584
Leu Leu Ser Thr Glu Gly Gln Glu Met Val Phe Thr Gly Glu Ile Ile
        515                 520                 525 ggt ata gtt caa cca gaa aca ctc agc tca tcc aaa gta gta tgg gca      1632
Gly Ile Val Gln Pro Glu Thr Leu Ser Ser Ser Lys Val Val Trp Ala
530                 535                 540 tcg ttt tgg gca aaa agg aaa aac ggc tta tta gtt tgt gtt ttc gaa      1680
Ser Phe Trp Ala Lys Arg Lys Asn Gly Leu Leu Val Cys Val Phe Glu
545                 550                 555                 560 aag gtt cct tgc gat tat gtt gat gta ctt ttg aac ctg gat gat ttt      1728
Lys Val Pro Cys Asp Tyr Val Asp Val Leu Leu Asn Leu Asp Asp Phe
                565                 570                 575 ggg gcc gag aat att gta gac aaa tgt gag tta tta tca gat gga ccc      1776
Gly Ala Glu Asn Ile Val Asp Lys Cys Glu Leu Leu Ser Asp Gly Pro
            580                 585                 590 aca ttg tct tcc tct tct aca tta tcg cta cct aag atg gct tct tca      1824
```

```
                      -continued

Thr Leu Ser Ser Ser Thr Leu Ser Leu Pro Lys Met Ala Ser Ser
        595                 600             605 cca act ggt agt aaa tta gag tat tcg ttg gag agg aaa atc ctg gaa      1872
Pro Thr Gly Ser Lys Leu Glu Tyr Ser Leu Glu Arg Lys Ile Leu Glu
    610                 615             620 aag agt tat act aag cct act tca aca gag aat cgc aac ggc gat gaa      1920
Lys Ser Tyr Thr Lys Pro Thr Ser Thr Glu Asn Arg Asn Gly Asp Glu
625                 630             635                 640 aac caa ctt gat gga gat agt cat tct gaa cca tcg ctg tca tca tcg      1968
Asn Gln Leu Asp Gly Asp Ser His Ser Glu Pro Ser Leu Ser Ser Ser
                645             650                 655 cca gta agg tcg aag aaa agt gta aag ttc gca aat gat att aaa gac      2016
Pro Val Arg Ser Lys Lys Ser Val Lys Phe Ala Asn Asp Ile Lys Asp
            660             665             670 gtc aag agt ata agc caa tcg tta gcc aaa tta atg gat gat gtg agg      2064
Val Lys Ser Ile Ser Gln Ser Leu Ala Lys Leu Met Asp Asp Val Arg
        675             680             685 aat ggg gtt gta ttt gat ccc gat gac gac ctt ttg cct atg ccc atc      2112
Asn Gly Val Val Phe Asp Pro Asp Asp Asp Leu Leu Pro Met Pro Ile
    690             695             700 aaa gtt tgc aac cac att aat gaa aca aga tat ttt act cta aat cat      2160
Lys Val Cys Asn His Ile Asn Glu Thr Arg Tyr Phe Thr Leu Asn His
705             710             715                 720 cta tct tat aat atc cca tgc gcg gtt tcc tcc act gtg ttg gag gat      2208
Leu Ser Tyr Asn Ile Pro Cys Ala Val Ser Ser Thr Val Leu Glu Asp
                725             730                 735 gag ctg aaa tta aag att cac agt tta cct tac cag gcg ggt ttg ttt      2256
Glu Leu Lys Leu Lys Ile His Ser Leu Pro Tyr Gln Ala Gly Leu Phe
            740             745             750 att gtg gat tcg cat act tta gat att gta agt tcc aat aaa tct att      2304
Ile Val Asp Ser His Thr Leu Asp Ile Val Ser Ser Asn Lys Ser Ile
        755             760             765 tta aaa aac atg ttt ggt tat cat ttt gct gag ctg gtg gga aaa tcc      2352
Leu Lys Asn Met Phe Gly Tyr His Phe Ala Glu Leu Val Gly Lys Ser
    770             775             780 att act gaa ata att cct tct ttc cca aaa ttc ctc caa ttt ata aat      2400
Ile Thr Glu Ile Ile Pro Ser Phe Pro Lys Phe Leu Gln Phe Ile Asn
785             790             795                 800 gac aaa tat cct gcg ttg gat atc aca ctc cat aaa aat aaa ggt ttg      2448
Asp Lys Tyr Pro Ala Leu Asp Ile Thr Leu His Lys Asn Lys Gly Leu
                805             810                 815 gta tta aca gaa cat ttt ttt agg aaa att cag gca gag att atg ggt      2496
Val Leu Thr Glu His Phe Phe Arg Lys Ile Gln Ala Glu Ile Met Gly
            820             825             830 gat cgt aaa agc ttt tat acg tcg gtg ggt att gat ggc ctt cat agg      2544
Asp Arg Lys Ser Phe Tyr Thr Ser Val Gly Ile Asp Gly Leu His Arg
        835             840             845 gat ggc tgt gaa atc aaa att gat ttc cag ctg cgt gtc atg aat tct      2592
Asp Gly Cys Glu Ile Lys Ile Asp Phe Gln Leu Arg Val Met Asn Ser
850             855             860 aaa gtg att ttg ctt tgg gtt aca cat tcg aga gac gtg gta ttt gaa      2640
Lys Val Ile Leu Leu Trp Val Thr His Ser Arg Asp Val Val Phe Glu
865             870             875                 880 gaa tat aat aca aat cca tct caa ttg aag atg ctg aag gag agt gaa      2688
Glu Tyr Asn Thr Asn Pro Ser Gln Leu Lys Met Leu Lys Glu Ser Glu
                885             890                 895 tta agt tta atg agc agt gca agt agt tct gcc agc tct tcc aaa aaa      2736
Leu Ser Leu Met Ser Ser Ala Ser Ser Ala Ser Ser Lys Lys
            900             905             910
```

|     |     |
| --- | --- |
| tct tcg tct agg ata tcc acc ggg aca tta aag gac atg agt aat ctg<br>Ser Ser Ser Arg Ile Ser Thr Gly Thr Leu Lys Asp Met Ser Asn Leu<br>        915                     920                   925 | 2784 |
| tca aca tat gag gat ttg gcc cac cga acg aat aag ctt aag tat gaa<br>Ser Thr Tyr Glu Asp Leu Ala His Arg Thr Asn Lys Leu Lys Tyr Glu<br>        930                     935                   940 | 2832 |
| atc gga gat gat tct aga gca cat tct caa tct act ttg tcc gag cag<br>Ile Gly Asp Asp Ser Arg Ala His Ser Gln Ser Thr Leu Ser Glu Gln<br>945                   950                   955                   960 | 2880 |
| gaa caa gtt ccc ctg gaa aac gat aag gac agt ggc gag atg atg ctt<br>Glu Gln Val Pro Leu Glu Asn Asp Lys Asp Ser Gly Glu Met Met Leu<br>                965                   970                   975 | 2928 |
| gca gac ccc gaa atg aag cac aag tta gaa ttg gcc aga att tac tca<br>Ala Asp Pro Glu Met Lys His Lys Leu Glu Leu Ala Arg Ile Tyr Ser<br>        980                     985                   990 | 2976 |
| aga gat aaa tct caa ttt gtg aaa gaa gga aat ttt aaa gtt gac gaa<br>Arg Asp Lys Ser Gln Phe Val Lys Glu Gly Asn Phe Lys Val Asp Glu<br>                995                   1000                 1005 | 3024 |
| aat ttg att att agc aaa att tca ctt tcc cca agc act gaa tcc<br>Asn Leu Ile Ile Ser Lys Ile Ser Leu Ser Pro Ser Thr Glu Ser<br>      1010                   1015                 1020 | 3069 |
| tta gca gat tct aaa agt tct ggg aaa ggg ctt tct cca ctt gaa<br>Leu Ala Asp Ser Lys Ser Ser Gly Lys Gly Leu Ser Pro Leu Glu<br>      1025                   1030                 1035 | 3114 |
| gag gaa aag cta att gac gaa aac gct aca gaa aac gga tta gcg<br>Glu Glu Lys Leu Ile Asp Glu Asn Ala Thr Glu Asn Gly Leu Ala<br>      1040                   1045                 1050 | 3159 |
| gga tca cct aaa gac gaa gac gga atc ata atg act aac aag cga<br>Gly Ser Pro Lys Asp Glu Asp Gly Ile Ile Met Thr Asn Lys Arg<br>      1055                   1060                 1065 | 3204 |
| gga aac caa cct gtt agt act ttc cta cgc acc ccc gaa aag aac<br>Gly Asn Gln Pro Val Ser Thr Phe Leu Arg Thr Pro Glu Lys Asn<br>      1070                   1075                 1080 | 3249 |
| atc ggt gct caa aag cat gtt aag aag ttt tcg gac ttc gta agt<br>Ile Gly Ala Gln Lys His Val Lys Lys Phe Ser Asp Phe Val Ser<br>      1085                   1090                 1095 | 3294 |
| ctg caa aaa atg ggt gaa ggt gca tat ggt aag gtc aac cta tgt<br>Leu Gln Lys Met Gly Glu Gly Ala Tyr Gly Lys Val Asn Leu Cys<br>      1100                   1105                 1110 | 3339 |
| att cat aag aag aat agg tat att gtg gtg att aag atg att ttt<br>Ile His Lys Lys Asn Arg Tyr Ile Val Val Ile Lys Met Ile Phe<br>      1115                   1120                 1125 | 3384 |
| aaa gaa aga atc ctt gta gat aca tgg gtt aga gat agg aaa tta<br>Lys Glu Arg Ile Leu Val Asp Thr Trp Val Arg Asp Arg Lys Leu<br>      1130                   1135                 1140 | 3429 |
| ggc act ata cct tct gag atc caa att atg gcc acg ttg aac aaa<br>Gly Thr Ile Pro Ser Glu Ile Gln Ile Met Ala Thr Leu Asn Lys<br>      1145                   1150                 1155 | 3474 |
| aaa cca cat gag aat att tta cgg tta ctg gat ttt ttt gaa gac<br>Lys Pro His Glu Asn Ile Leu Arg Leu Leu Asp Phe Phe Glu Asp<br>      1160                   1165                 1170 | 3519 |
| gac gat tac tat tat atc gaa act ccc gta cat ggt gaa aca gga<br>Asp Asp Tyr Tyr Tyr Ile Glu Thr Pro Val His Gly Glu Thr Gly<br>      1175                   1180                 1185 | 3564 |
| tgt ata gat ctt ttc gat cta att gaa ttt aaa acc aac atg acc<br>Cys Ile Asp Leu Phe Asp Leu Ile Glu Phe Lys Thr Asn Met Thr<br>      1190                   1195                 1200 | 3609 |
| gaa ttt gaa gca aaa ttg ata ttc aag cag gtt gta gcg gga ata<br>Glu Phe Glu Ala Lys Leu Ile Phe Lys Gln Val Val Ala Gly Ile<br>      1205                   1210                 1215 | 3654 |

-continued

```
aaa cat cta cac gac cag ggt att gtt cac aga gat atc aag gat      3699
Lys His Leu His Asp Gln Gly Ile Val His Arg Asp Ile Lys Asp
    1220                1225                1230 gag aat gtt atc gta gat tct aaa ggc ttt gtt aag att att gat      3744
Glu Asn Val Ile Val Asp Ser Lys Gly Phe Val Lys Ile Ile Asp
1235                1240                1245 ttt gga tct gct gcg tat gtc aaa agc gga cca ttt gat gtt ttt      3789
Phe Gly Ser Ala Ala Tyr Val Lys Ser Gly Pro Phe Asp Val Phe
    1250                1255                1260 gtt ggg aca ata gat tat gct gcc cct gaa gtc tta gga gga aac      3834
Val Gly Thr Ile Asp Tyr Ala Ala Pro Glu Val Leu Gly Gly Asn
1265                1270                1275 cct tat gag ggc caa cca cag gat att tgg gct att ggt att cta      3879
Pro Tyr Glu Gly Gln Pro Gln Asp Ile Trp Ala Ile Gly Ile Leu
    1280                1285                1290 ttg tat acg gtg gtc ttc aaa gaa aac ccc ttc tac aat ata gat      3924
Leu Tyr Thr Val Val Phe Lys Glu Asn Pro Phe Tyr Asn Ile Asp
1295                1300                1305 gaa ata tta gaa ggc gac ctg aaa ttc aat aat gca gag gaa gtt      3969
Glu Ile Leu Glu Gly Asp Leu Lys Phe Asn Asn Ala Glu Glu Val
    1310                1315                1320 agt gaa gat tgc att gag tta atc aag agt att ttg aac cgt tgc      4014
Ser Glu Asp Cys Ile Glu Leu Ile Lys Ser Ile Leu Asn Arg Cys
1325                1330                1335 gta ccg aag aga ccc acc att gac gac ata aat aac gac aaa tgg      4059
Val Pro Lys Arg Pro Thr Ile Asp Asp Ile Asn Asn Asp Lys Trp
    1340                1345                1350 ttg gtt att tga                                                   4071
Leu Val Ile
    1355

<210> SEQ ID NO 6
<211> LENGTH: 1356
<212> TYPE: PRT
<213> ORGANISM: yeast

<400> SEQUENCE: 6

Met Pro Tyr Ile Gly Ala Ser Asn Leu Ser Glu His Ser Phe Val Asn
1               5                   10                  15

Leu Lys Glu Lys His Ala Ile Thr His Lys Gly Thr Ser Ser Ser Val
                20                  25                  30

Ala Ser Leu Gln Thr Pro Pro Ser Pro Asp Gln Glu Asn His Ile Asp
            35                  40                  45

Asn Glu Leu Glu Asn Tyr Asp Thr Ser Leu Ser Asp Val Ser Thr Pro
        50                  55                  60

Asn Lys Lys Glu Gly Asp Glu Phe Gln Gln Ser Leu Arg Asp Thr Phe
65                  70                  75                  80

Ala Ser Phe Arg Lys Thr Lys Pro Pro Pro Leu Asp Phe Glu Gln
                85                  90                  95

Pro Arg Leu Pro Ser Thr Ala Ser Ser Val Asp Ser Thr Val Ser
            100                 105                 110

Ser Pro Leu Thr Asp Glu Asp Ile Lys Glu Leu Glu Phe Leu Pro Asn
        115                 120                 125

Glu Ser Thr His Ser Tyr Ser Tyr Asn Pro Leu Ser Pro Asn Ser Leu
    130                 135                 140

Ala Val Arg Leu Arg Ile Leu Lys Arg Ser Leu Glu Ile Ile Ile Gln
145                 150                 155                 160
```

-continued

```
Asn Pro Ser Met Leu Leu Glu Pro Thr Pro Asp Asp Leu Pro Pro Leu
            165                 170                 175

Lys Glu Phe Ala Gly Arg Arg Ser Ser Leu Pro Arg Thr Ser Ala Ser
            180                 185                 190

Ala Asn His Leu Met Asn Arg Asn Lys Ser Gln Ile Trp Asn Thr Thr
            195                 200                 205

Ser Ala Thr Leu Asn Ala Phe Val Asn Asn Thr Ser Ser Ser Ser Ala
            210                 215                 220

Ala Ser Ser Ala Leu Ser Asn Lys Lys Pro Gly Thr Pro Val Phe Pro
225                 230                 235                 240

Asn Leu Asp Pro Thr His Ser Gln Thr Phe His Arg Ala Asn Ser Leu
            245                 250                 255

Ala Tyr Leu Pro Ser Ile Leu Pro Glu Gln Asp Pro Leu Leu Lys His
            260                 265                 270

Asn Asn Ser Leu Phe Arg Gly Asp Tyr Gly Asn Asn Ile Ser Pro Glu
            275                 280                 285

Arg Pro Ser Phe Arg Gln Pro Phe Lys Asp Gln Thr Ser Asn Leu Arg
            290                 295                 300

Asn Ser Ser Leu Leu Asn Glu Arg Ala Tyr Gln Glu Asp Glu Thr Phe
305                 310                 315                 320

Leu Pro His His Gly Pro Ser Met Asp Leu Leu Asn Glu Gln Arg Ala
            325                 330                 335

Asn Leu Lys Ser Leu Leu Asn Leu Leu Asn Glu Thr Leu Glu Lys Asn
            340                 345                 350

Thr Ser Glu Arg Ala Ser Asp Leu His Met Ile Ser Leu Phe Asn Leu
            355                 360                 365

Asn Lys Leu Met Leu Gly Asp Pro Lys Lys Asn Asn Ser Glu Arg Asp
            370                 375                 380

Lys Arg Thr Glu Lys Leu Lys Lys Ile Leu Leu Asp Ser Leu Ala Glu
385                 390                 395                 400

Pro Phe Phe Glu His Tyr Asn Phe Ile Gly Asp Asn Pro Ile Ala Asp
            405                 410                 415

Thr Asp Glu Leu Lys Glu Glu Ile Asp Glu Phe Thr Gly Ser Gly Asp
            420                 425                 430

Thr Thr Ala Ile Thr Asp Ile Arg Pro Gln Gln Asp Tyr Gly Arg Ile
            435                 440                 445

Leu Arg Thr Phe Thr Ser Thr Lys Asn Ser Ala Pro Gln Ala Ile Phe
            450                 455                 460

Thr Cys Ser Gln Glu Asp Pro Trp Gln Phe Arg Ala Ala Asn Asp Leu
465                 470                 475                 480

Ala Cys Leu Val Phe Gly Ile Ser Gln Asn Ala Ile Arg Ala Leu Thr
            485                 490                 495

Leu Met Asp Leu Ile His Thr Ser Arg Asn Phe Val Leu His Lys
            500                 505                 510

Leu Leu Ser Thr Glu Gly Gln Glu Met Val Phe Thr Gly Glu Ile Ile
            515                 520                 525

Gly Ile Val Gln Pro Glu Thr Leu Ser Ser Ser Lys Val Val Trp Ala
            530                 535                 540

Ser Phe Trp Ala Lys Arg Lys Asn Gly Leu Leu Val Cys Val Phe Glu
545                 550                 555                 560

Lys Val Pro Cys Asp Tyr Val Asp Val Leu Leu Asn Leu Asp Asp Phe
            565                 570                 575

Gly Ala Glu Asn Ile Val Asp Lys Cys Glu Leu Leu Ser Asp Gly Pro
```

-continued

```
                580                 585                 590
Thr Leu Ser Ser Ser Thr Leu Ser Leu Pro Lys Met Ala Ser Ser
            595                 600                 605
Pro Thr Gly Ser Lys Leu Glu Tyr Ser Leu Glu Arg Lys Ile Leu Glu
    610                 615                 620
Lys Ser Tyr Thr Lys Pro Thr Ser Thr Glu Asn Arg Asn Gly Asp Glu
625                 630                 635                 640
Asn Gln Leu Asp Gly Asp Ser His Ser Glu Pro Ser Leu Ser Ser Ser
                645                 650                 655
Pro Val Arg Ser Lys Lys Ser Val Lys Phe Ala Asn Asp Ile Lys Asp
            660                 665                 670
Val Lys Ser Ile Ser Gln Ser Leu Ala Lys Leu Met Asp Asp Val Arg
        675                 680                 685
Asn Gly Val Val Phe Asp Pro Asp Asp Leu Leu Pro Met Pro Ile
    690                 695                 700
Lys Val Cys Asn His Ile Asn Glu Thr Arg Tyr Phe Thr Leu Asn His
705                 710                 715                 720
Leu Ser Tyr Asn Ile Pro Cys Ala Val Ser Ser Thr Val Leu Glu Asp
                725                 730                 735
Glu Leu Lys Leu Lys Ile His Ser Leu Pro Tyr Gln Ala Gly Leu Phe
            740                 745                 750
Ile Val Asp Ser His Thr Leu Asp Ile Val Ser Ser Asn Lys Ser Ile
        755                 760                 765
Leu Lys Asn Met Phe Gly Tyr His Phe Ala Glu Leu Val Gly Lys Ser
    770                 775                 780
Ile Thr Glu Ile Ile Pro Ser Phe Pro Lys Phe Leu Gln Phe Ile Asn
785                 790                 795                 800
Asp Lys Tyr Pro Ala Leu Asp Ile Thr Leu His Lys Asn Lys Gly Leu
                805                 810                 815
Val Leu Thr Glu His Phe Phe Arg Lys Ile Gln Ala Glu Ile Met Gly
            820                 825                 830
Asp Arg Lys Ser Phe Tyr Thr Ser Val Gly Ile Asp Gly Leu His Arg
        835                 840                 845
Asp Gly Cys Glu Ile Lys Ile Asp Phe Gln Leu Arg Val Met Asn Ser
    850                 855                 860
Lys Val Ile Leu Leu Trp Val Thr His Ser Arg Asp Val Val Phe Glu
865                 870                 875                 880
Glu Tyr Asn Thr Asn Pro Ser Gln Leu Lys Met Leu Lys Glu Ser Glu
                885                 890                 895
Leu Ser Leu Met Ser Ser Ala Ser Ser Ala Ser Ser Ser Lys Lys
            900                 905                 910
Ser Ser Ser Arg Ile Ser Thr Gly Thr Leu Lys Asp Met Ser Asn Leu
        915                 920                 925
Ser Thr Tyr Glu Asp Leu Ala His Arg Thr Asn Lys Leu Lys Tyr Glu
    930                 935                 940
Ile Gly Asp Asp Ser Arg Ala His Ser Gln Ser Thr Leu Ser Glu Gln
945                 950                 955                 960
Glu Gln Val Pro Leu Glu Asn Asp Lys Asp Ser Gly Glu Met Met Leu
                965                 970                 975
Ala Asp Pro Glu Met Lys His Lys Leu Glu Leu Ala Arg Ile Tyr Ser
            980                 985                 990
Arg Asp Lys Ser Gln Phe Val Lys  Glu Gly Asn Phe Lys  Val Asp Glu
    995                 1000                 1005
```

```
Asn Leu Ile Ile Ser Lys Ile Ser Leu Ser Pro Ser Thr Glu Ser
    1010                1015                1020

Leu Ala Asp Ser Lys Ser Ser Gly Lys Gly Leu Ser Pro Leu Glu
    1025                1030                1035

Glu Glu Lys Leu Ile Asp Glu Asn Ala Thr Glu Asn Gly Leu Ala
    1040                1045                1050

Gly Ser Pro Lys Asp Glu Asp Gly Ile Ile Met Thr Asn Lys Arg
    1055                1060                1065

Gly Asn Gln Pro Val Ser Thr Phe Leu Arg Thr Pro Glu Lys Asn
    1070                1075                1080

Ile Gly Ala Gln Lys His Val Lys Lys Phe Ser Asp Phe Val Ser
    1085                1090                1095

Leu Gln Lys Met Gly Glu Gly Ala Tyr Gly Lys Val Asn Leu Cys
    1100                1105                1110

Ile His Lys Lys Asn Arg Tyr Ile Val Val Ile Lys Met Ile Phe
    1115                1120                1125

Lys Glu Arg Ile Leu Val Asp Thr Trp Val Arg Asp Arg Lys Leu
    1130                1135                1140

Gly Thr Ile Pro Ser Glu Ile Gln Ile Met Ala Thr Leu Asn Lys
    1145                1150                1155

Lys Pro His Glu Asn Ile Leu Arg Leu Leu Asp Phe Phe Glu Asp
    1160                1165                1170

Asp Asp Tyr Tyr Tyr Ile Glu Thr Pro Val His Gly Glu Thr Gly
    1175                1180                1185

Cys Ile Asp Leu Phe Asp Leu Ile Glu Phe Lys Thr Asn Met Thr
    1190                1195                1200

Glu Phe Glu Ala Lys Leu Ile Phe Lys Gln Val Val Ala Gly Ile
    1205                1210                1215

Lys His Leu His Asp Gln Gly Ile Val His Arg Asp Ile Lys Asp
    1220                1225                1230

Glu Asn Val Ile Val Asp Ser Lys Gly Phe Val Lys Ile Ile Asp
    1235                1240                1245

Phe Gly Ser Ala Ala Tyr Val Lys Ser Gly Pro Phe Asp Val Phe
    1250                1255                1260

Val Gly Thr Ile Asp Tyr Ala Ala Pro Glu Val Leu Gly Gly Asn
    1265                1270                1275

Pro Tyr Glu Gly Gln Pro Gln Asp Ile Trp Ala Ile Gly Ile Leu
    1280                1285                1290

Leu Tyr Thr Val Val Phe Lys Glu Asn Pro Phe Tyr Asn Ile Asp
    1295                1300                1305

Glu Ile Leu Glu Gly Asp Leu Lys Phe Asn Asn Ala Glu Glu Val
    1310                1315                1320

Ser Glu Asp Cys Ile Glu Leu Ile Lys Ser Ile Leu Asn Arg Cys
    1325                1330                1335

Val Pro Lys Arg Pro Thr Ile Asp Asp Ile Asn Asn Asp Lys Trp
    1340                1345                1350

Leu Val Ile
    1355

<210> SEQ ID NO 7
<211> LENGTH: 3306
<212> TYPE: DNA
<213> ORGANISM: yeast
<220> FEATURE:
```

-continued

<221> NAME/KEY: CDS
<222> LOCATION: (1)..(3303)

<400> SEQUENCE: 7

| atg aca tac ccg gtt agt gca gcc gct cct gcc gac att tca tat tct | 48 |
|---|---|
| Met Thr Tyr Pro Val Ser Ala Ala Ala Pro Ala Asp Ile Ser Tyr Ser | |
| 1               5                   10                  15 | |

| aaa aat acc ccg ttg gta ggg ctc tct aaa cct cca tgc ttg tac caa | 96 |
|---|---|
| Lys Asn Thr Pro Leu Val Gly Leu Ser Lys Pro Pro Cys Leu Tyr Gln | |
|             20                  25                  30 | |

| cac gct tcc tcg tcc gtc gat tcg ttt tcg tca aca ttc agt gat gat | 144 |
|---|---|
| His Ala Ser Ser Ser Val Asp Ser Phe Ser Ser Thr Phe Ser Asp Asp | |
|         35                  40                  45 | |

| gat cgt tcg gac ctt gtt gct gta cct aat gag tcg ccg cat gca ttt | 192 |
|---|---|
| Asp Arg Ser Asp Leu Val Ala Val Pro Asn Glu Ser Pro His Ala Phe | |
| 50                  55                  60 | |

| tcg tat aat ccc ata tca cca aac tca ctg gga gta agg ttg acc atc | 240 |
|---|---|
| Ser Tyr Asn Pro Ile Ser Pro Asn Ser Leu Gly Val Arg Leu Thr Ile | |
| 65              70                  75                  80 | |

| tta aga agg tct ttg gaa ata atg gta aac agt cct gac atc tta cat | 288 |
|---|---|
| Leu Arg Arg Ser Leu Glu Ile Met Val Asn Ser Pro Asp Ile Leu His | |
|             85                  90                  95 | |

| gag ttg aag aaa aaa gca ccc gta ata gca tac ccc ccc tca ctt aga | 336 |
|---|---|
| Glu Leu Lys Lys Lys Ala Pro Val Ile Ala Tyr Pro Pro Ser Leu Arg | |
|         100                 105                 110 | |

| cac aca aga aac tta aca gag act gcc acg tta tca gca tcg cga gat | 384 |
|---|---|
| His Thr Arg Asn Leu Thr Glu Thr Ala Thr Leu Ser Ala Ser Arg Asp | |
|     115                 120                 125 | |

| ccg tta aat ggg tct cta att tca cca tta gta tcc aat atg cca tct | 432 |
|---|---|
| Pro Leu Asn Gly Ser Leu Ile Ser Pro Leu Val Ser Asn Met Pro Ser | |
| 130                 135                 140 | |

| cct gct agt aga ccc gtg ata cag aga gca acg tcc tta atg gtg ttg | 480 |
|---|---|
| Pro Ala Ser Arg Pro Val Ile Gln Arg Ala Thr Ser Leu Met Val Leu | |
| 145                 150                 155                 160 | |

| cct gat aat gat act gcc agt aaa ctg aat cca gcc aag tcc gag tta | 528 |
|---|---|
| Pro Asp Asn Asp Thr Ala Ser Lys Leu Asn Pro Ala Lys Ser Glu Leu | |
|             165                 170                 175 | |

| gaa aac ttg tta ttc ttg cta aat tta gca ttg gaa aac aat tcc ttc | 576 |
|---|---|
| Glu Asn Leu Leu Phe Leu Leu Asn Leu Ala Leu Glu Asn Asn Ser Phe | |
|         180                 185                 190 | |

| gaa aga gct tcc gat tta cac atg cta tcg tta ttg aat atc aag aaa | 624 |
|---|---|
| Glu Arg Ala Ser Asp Leu His Met Leu Ser Leu Leu Asn Ile Lys Lys | |
|     195                 200                 205 | |

| ata aac ttt gat tca gac att caa aaa tca gaa act ttg aaa aag gtt | 672 |
|---|---|
| Ile Asn Phe Asp Ser Asp Ile Gln Lys Ser Glu Thr Leu Lys Lys Val | |
| 210                 215                 220 | |

| tta tta gat agt tta gca gaa cca ttt ttt gaa aac tac aag aag ttc | 720 |
|---|---|
| Leu Leu Asp Ser Leu Ala Glu Pro Phe Phe Glu Asn Tyr Lys Lys Phe | |
| 225                 230                 235                 240 | |

| cct cac aaa gat tta ggt tcg aaa tcg caa tat aat gaa tat gag gag | 768 |
|---|---|
| Pro His Lys Asp Leu Gly Ser Lys Ser Gln Tyr Asn Glu Tyr Glu Glu | |
|             245                 250                 255 | |

| aaa cac gat gat ata gtc tcc tta gca gac atc aaa cca caa cag gac | 816 |
|---|---|
| Lys His Asp Asp Ile Val Ser Leu Ala Asp Ile Lys Pro Gln Gln Asp | |
|         260                 265                 270 | |

| tat agc cga att ctt cat cct ttc aca tct gca aaa aat tct ggt cca | 864 |
|---|---|
| Tyr Ser Arg Ile Leu His Pro Phe Thr Ser Ala Lys Asn Ser Gly Pro | |
|     275                 280                 285 | |

| gag gcc att ttt aca tgt tct caa caa tac ccc tgg aac ttc aaa gct | 912 |
|---|---|
| Glu Ala Ile Phe Thr Cys Ser Gln Gln Tyr Pro Trp Asn Phe Lys Ala | |

```
              290                 295                 300
gcc aat gat ttg gcg tgt cta acg ttc ggt ata tca aag aat gtt atc        960
Ala Asn Asp Leu Ala Cys Leu Thr Phe Gly Ile Ser Lys Asn Val Ile
305                 310                 315                 320 aag gca ctt act tta cta gac ctt att cat acg gat agc aga aat ttt       1008
Lys Ala Leu Thr Leu Leu Asp Leu Ile His Thr Asp Ser Arg Asn Phe
                325                 330                 335 gtt cta gag aaa atc atg aat gca gaa gat gat aac caa gaa att gtg       1056
Val Leu Glu Lys Ile Met Asn Ala Glu Asp Asp Asn Gln Glu Ile Val
            340                 345                 350 ttt acc gga gaa act ata cct atc gtc cag cca aat tcg aca agc aat       1104
Phe Thr Gly Glu Thr Ile Pro Ile Val Gln Pro Asn Ser Thr Ser Asn
        355                 360                 365 aat aat gta cca aat ctg att tgg gct tca cta tgg gcc aag cgg aag       1152
Asn Asn Val Pro Asn Leu Ile Trp Ala Ser Leu Trp Ala Lys Arg Lys
370                 375                 380 aat ggc cta ctg gtc tgc gta ttt gaa aaa acg cct tgc gat tac att       1200
Asn Gly Leu Leu Val Cys Val Phe Glu Lys Thr Pro Cys Asp Tyr Ile
385                 390                 395                 400 gac gtc atg tta aac ttg aga gat ttt tca gtg gac agc att att gat       1248
Asp Val Met Leu Asn Leu Arg Asp Phe Ser Val Asp Ser Ile Ile Asp
                405                 410                 415 aca aca cac ttt ctg gaa aac ttt gac aag aaa aag cag caa gaa tca       1296
Thr Thr His Phe Leu Glu Asn Phe Asp Lys Lys Lys Gln Gln Glu Ser
            420                 425                 430 act tcg cca atg aca gaa aag aaa acg gta aaa ttt gca aat gaa att       1344
Thr Ser Pro Met Thr Glu Lys Lys Thr Val Lys Phe Ala Asn Glu Ile
        435                 440                 445 cac gat att ggg tca gta agt cac tca ctg agt aaa cta att gat gat       1392
His Asp Ile Gly Ser Val Ser His Ser Leu Ser Lys Leu Ile Asp Asp
450                 455                 460 gta cgt ttt gga aaa gtg ttt tct gca gat gat gat tta tta ccc ttg       1440
Val Arg Phe Gly Lys Val Phe Ser Ala Asp Asp Asp Leu Leu Pro Leu
465                 470                 475                 480 tct atc agg gtg gca aat cat gtc aac gaa gag aga tat ttt acg ttg       1488
Ser Ile Arg Val Ala Asn His Val Asn Glu Glu Arg Tyr Phe Thr Leu
                485                 490                 495 aat tgt cta tct gaa aat ata cca tgt gct gtt aca act tcc gta ttg       1536
Asn Cys Leu Ser Glu Asn Ile Pro Cys Ala Val Thr Thr Ser Val Leu
            500                 505                 510 gaa aac gaa ata aaa tta aaa att cat agt ttg ccc tat cag gct ggg       1584
Glu Asn Glu Ile Lys Leu Lys Ile His Ser Leu Pro Tyr Gln Ala Gly
        515                 520                 525 cta ttt att gtt gac agt cac act tta agt ctt tta agt ttc aac aaa       1632
Leu Phe Ile Val Asp Ser His Thr Leu Ser Leu Leu Ser Phe Asn Lys
530                 535                 540 tca gtc gcc aaa aac atg ttt ggc ttg cga ctt cac gag ttg gcc ggt       1680
Ser Val Ala Lys Asn Met Phe Gly Leu Arg Leu His Glu Leu Ala Gly
545                 550                 555                 560 agt tcg gtt act aag ttg gtt cct tct ttg gcg gac atg ata tct tat       1728
Ser Ser Val Thr Lys Leu Val Pro Ser Leu Ala Asp Met Ile Ser Tyr
                565                 570                 575 atc aat aaa act tat cct atg tta aat atc aca tta cca gaa aat aaa       1776
Ile Asn Lys Thr Tyr Pro Met Leu Asn Ile Thr Leu Pro Glu Asn Lys
            580                 585                 590 gga ttg gtt tta aca gaa cat ttt ttc aga aaa att gag gct gaa atg       1824
Gly Leu Val Leu Thr Glu His Phe Phe Arg Lys Ile Glu Ala Glu Met
        595                 600                 605 cat cat gat aag gac tcg ttt tac act tct att ggt cta gac ggc tgt       1872
```

-continued

```
                His His Asp Lys Asp Ser Phe Tyr Thr Ser Ile Gly Leu Asp Gly Cys
                            610                 615                 620 cac aaa gat ggt aat ttg ata aag gtg gat gtt caa tta cgg gtc ttg        1920
His Lys Asp Gly Asn Leu Ile Lys Val Asp Val Gln Leu Arg Val Leu
625                 630                 635                 640 aat acg aat gct gta tta tta tgg att aca cac tca aga gac gtg gtc        1968
Asn Thr Asn Ala Val Leu Leu Trp Ile Thr His Ser Arg Asp Val Val
                645                 650                 655 att gaa aat tat acc acc gtt cct tcg cag cta ccg atg tta aag gag        2016
Ile Glu Asn Tyr Thr Thr Val Pro Ser Gln Leu Pro Met Leu Lys Glu
            660                 665                 670 aac gaa att gat gtc gtt ggc agt aga ggt agt tcc agt gca tct tcc        2064
Asn Glu Ile Asp Val Val Gly Ser Arg Gly Ser Ser Ser Ala Ser Ser
            675                 680                 685 aag aaa tct tcg gaa aaa att cct gtg aat act ttg aag gca atg gct        2112
Lys Lys Ser Ser Glu Lys Ile Pro Val Asn Thr Leu Lys Ala Met Ala
690                 695                 700 gat ctg tcg att agc tcc gct gaa acg att tct aat tca gac gat gaa        2160
Asp Leu Ser Ile Ser Ser Ala Glu Thr Ile Ser Asn Ser Asp Asp Glu
705                 710                 715                 720 gta gac tta aat caa gtg aat gaa aaa cta cga gaa act tct tgc ggt        2208
Val Asp Leu Asn Gln Val Asn Glu Lys Leu Arg Glu Thr Ser Cys Gly
                725                 730                 735 aaa gtg aga ggt atc gaa tct aat gac aac aat aac tat gac gat gac        2256
Lys Val Arg Gly Ile Glu Ser Asn Asp Asn Asn Asn Tyr Asp Asp Asp
            740                 745                 750 atg aca atg gtt gat gat cct gag tta aaa cat aaa att gaa tta acg        2304
Met Thr Met Val Asp Asp Pro Glu Leu Lys His Lys Ile Glu Leu Thr
            755                 760                 765 aaa atg tac acg cag gac aaa tca aaa ttt gta aag gac gac aac ttt        2352
Lys Met Tyr Thr Gln Asp Lys Ser Lys Phe Val Lys Asp Asp Asn Phe
770                 775                 780 aaa gtg gat gaa aaa ttt ata atg agg ata att gaa ccg ata aac gga        2400
Lys Val Asp Glu Lys Phe Ile Met Arg Ile Ile Glu Pro Ile Asn Gly
785                 790                 795                 800 gaa gaa atc aaa aag gaa aca aat gag cta gac aaa aga aat tct act        2448
Glu Glu Ile Lys Lys Glu Thr Asn Glu Leu Asp Lys Arg Asn Ser Thr
                805                 810                 815 tta aaa gct acg tac ttg act act cca gag gct aat ata ggc tca caa        2496
Leu Lys Ala Thr Tyr Leu Thr Thr Pro Glu Ala Asn Ile Gly Ser Gln
            820                 825                 830 aag cgc ata aag aaa ttt tct gat ttt act att ctg caa gtg atg ggt        2544
Lys Arg Ile Lys Lys Phe Ser Asp Phe Thr Ile Leu Gln Val Met Gly
            835                 840                 845 gag ggt gcg tac ggt aaa gtc aat tta tgc att cat aac aga gaa cac        2592
Glu Gly Ala Tyr Gly Lys Val Asn Leu Cys Ile His Asn Arg Glu His
850                 855                 860 tat atc gtg gtc atc aaa atg att ttc aaa gag agg att tta gta gac        2640
Tyr Ile Val Val Ile Lys Met Ile Phe Lys Glu Arg Ile Leu Val Asp
865                 870                 875                 880 aca tgg gtg aga gat aga aaa tta ggt act ata cct tct gag atc caa        2688
Thr Trp Val Arg Asp Arg Lys Leu Gly Thr Ile Pro Ser Glu Ile Gln
                885                 890                 895 att atg gcg acc ttg aat aaa aat tcc caa gaa aat atc ttg aag tta        2736
Ile Met Ala Thr Leu Asn Lys Asn Ser Gln Glu Asn Ile Leu Lys Leu
            900                 905                 910 tta gat ttt ttt gaa gat gac gat tat tat tac att gaa aca ccg gtc        2784
Leu Asp Phe Phe Glu Asp Asp Asp Tyr Tyr Tyr Ile Glu Thr Pro Val
            915                 920                 925
```

| | | | | | | | | | | | | | | |
|---|---|---|---|---|---|---|---|---|---|---|---|---|---|---|
| cat | gga | gaa | act | ggt | agt | att | gat | cta | ttt | gat | gtt | atc | gaa ttc aaa | 2832 |
| His | Gly | Glu | Thr | Gly | Ser | Ile | Asp | Leu | Phe | Asp | Val | Ile | Glu Phe Lys | |
| | | 930 | | | | 935 | | | | 940 | | | | |
| aaa | gat | atg | gtt | gaa | cat | gaa | gct | aaa | ctg | gtg | ttt | aaa | cag gta gtc | 2880 |
| Lys | Asp | Met | Val | Glu | His | Glu | Ala | Lys | Leu | Val | Phe | Lys | Gln Val Val | |
| 945 | | | | | 950 | | | | 955 | | | | 960 | |
| gct | agt | ata | aag | cat | tta | cat | gac | caa | gga | att | gtt | cat | aga gac ata | 2928 |
| Ala | Ser | Ile | Lys | His | Leu | His | Asp | Gln | Gly | Ile | Val | His | Arg Asp Ile | |
| | | | | 965 | | | | 970 | | | | 975 | | |
| aag | gac | gaa | aat | gtt | att | gtt | gat | tct | cat | ggc | ttt | gta | aaa tta atc | 2976 |
| Lys | Asp | Glu | Asn | Val | Ile | Val | Asp | Ser | His | Gly | Phe | Val | Lys Leu Ile | |
| | | | 980 | | | | 985 | | | | 990 | | | |
| gat | ttc | ggt | tcg | gct | gcc | tat | atc | aag | agt | gga | cca | ttc | gat gtt ttt | 3024 |
| Asp | Phe | Gly | Ser | Ala | Ala | Tyr | Ile | Lys | Ser | Gly | Pro | Phe | Asp Val Phe | |
| | | | 995 | | | | 1000 | | | | 1005 | | | |
| gtg | gga | aca | atg | gac | tat | gct | gca | cct | gaa | gtc | ctt | ggt | ggt tcc | 3069 |
| Val | Gly | Thr | Met | Asp | Tyr | Ala | Ala | Pro | Glu | Val | Leu | Gly | Gly Ser | |
| | 1010 | | | | 1015 | | | | 1020 | | | | | |
| tct | tac | aaa | ggt | aaa | cca | caa | gat | att | tgg | gct | ctt | ggt | gtg cta | 3114 |
| Ser | Tyr | Lys | Gly | Lys | Pro | Gln | Asp | Ile | Trp | Ala | Leu | Gly | Val Leu | |
| | 1025 | | | | 1030 | | | | 1035 | | | | | |
| ctt | tat | acc | ata | att | tat | aaa | gag | aat | cct | tat | tac | aac | att gat | 3159 |
| Leu | Tyr | Thr | Ile | Ile | Tyr | Lys | Glu | Asn | Pro | Tyr | Tyr | Asn | Ile Asp | |
| | 1040 | | | | 1045 | | | | 1050 | | | | | |
| gaa | atc | ttg | gaa | ggt | gaa | tta | agg | ttc | gat | aaa | tcg | gaa | cat gtc | 3204 |
| Glu | Ile | Leu | Glu | Gly | Glu | Leu | Arg | Phe | Asp | Lys | Ser | Glu | His Val | |
| | 1055 | | | | 1060 | | | | 1065 | | | | | |
| agt | gaa | gaa | tgc | atc | agt | ttg | ata | aaa | aga | att | ttg | aca | aga gaa | 3249 |
| Ser | Glu | Glu | Cys | Ile | Ser | Leu | Ile | Lys | Arg | Ile | Leu | Thr | Arg Glu | |
| | 1070 | | | | 1075 | | | | 1080 | | | | | |
| gtt | gat | aaa | aga | cct | act | att | gat | gaa | ata | tat | gaa | gat | aaa tgg | 3294 |
| Val | Asp | Lys | Arg | Pro | Thr | Ile | Asp | Glu | Ile | Tyr | Glu | Asp | Lys Trp | |
| | 1085 | | | | 1090 | | | | 1095 | | | | | |
| ctt | aaa | atc | tag | | | | | | | | | | | 3306 |
| Leu | Lys | Ile | | | | | | | | | | | | |
| | 1100 | | | | | | | | | | | | | |

<210> SEQ ID NO 8
<211> LENGTH: 1101
<212> TYPE: PRT
<213> ORGANISM: yeast

<400> SEQUENCE: 8

Met Thr Tyr Pro Val Ser Ala Ala Pro Ala Asp Ile Ser Tyr Ser
1               5                   10                  15

Lys Asn Thr Pro Leu Val Gly Leu Ser Lys Pro Pro Cys Leu Tyr Gln
            20                  25                  30

His Ala Ser Ser Val Asp Ser Phe Ser Thr Phe Ser Asp Asp
        35                  40                  45

Asp Arg Ser Asp Leu Val Ala Val Pro Asn Glu Ser Pro His Ala Phe
    50                  55                  60

Ser Tyr Asn Pro Ile Ser Pro Asn Ser Leu Gly Val Arg Leu Thr Ile
65                  70                  75                  80

Leu Arg Arg Ser Leu Glu Ile Met Val Asn Ser Pro Asp Ile Leu His
                85                  90                  95

Glu Leu Lys Lys Lys Ala Pro Val Ile Ala Tyr Pro Pro Ser Leu Arg
            100                 105                 110

His Thr Arg Asn Leu Thr Glu Thr Ala Thr Leu Ser Ala Ser Arg Asp
        115                 120                 125

```
Pro Leu Asn Gly Ser Leu Ile Ser Pro Leu Val Ser Asn Met Pro Ser
    130                 135                 140

Pro Ala Ser Arg Pro Val Ile Gln Arg Ala Thr Ser Leu Met Val Leu
145                 150                 155                 160

Pro Asp Asn Asp Thr Ala Ser Lys Leu Asn Pro Ala Lys Ser Glu Leu
                165                 170                 175

Glu Asn Leu Leu Phe Leu Leu Asn Leu Ala Leu Glu Asn Asn Ser Phe
            180                 185                 190

Glu Arg Ala Ser Asp Leu His Met Leu Ser Leu Leu Asn Ile Lys Lys
        195                 200                 205

Ile Asn Phe Asp Ser Asp Ile Gln Lys Ser Glu Thr Leu Lys Lys Val
    210                 215                 220

Leu Leu Asp Ser Leu Ala Glu Pro Phe Phe Glu Asn Tyr Lys Lys Phe
225                 230                 235                 240

Pro His Lys Asp Leu Gly Ser Lys Ser Gln Tyr Asn Glu Tyr Glu Glu
                245                 250                 255

Lys His Asp Asp Ile Val Ser Leu Ala Asp Ile Lys Pro Gln Gln Asp
            260                 265                 270

Tyr Ser Arg Ile Leu His Pro Phe Thr Ser Ala Lys Asn Ser Gly Pro
        275                 280                 285

Glu Ala Ile Phe Thr Cys Ser Gln Gln Tyr Pro Trp Asn Phe Lys Ala
    290                 295                 300

Ala Asn Asp Leu Ala Cys Leu Thr Phe Gly Ile Ser Lys Asn Val Ile
305                 310                 315                 320

Lys Ala Leu Thr Leu Leu Asp Leu Ile His Thr Asp Ser Arg Asn Phe
                325                 330                 335

Val Leu Glu Lys Ile Met Asn Ala Glu Asp Asn Gln Glu Ile Val
            340                 345                 350

Phe Thr Gly Glu Thr Ile Pro Ile Val Gln Pro Asn Ser Thr Ser Asn
        355                 360                 365

Asn Asn Val Pro Asn Leu Ile Trp Ala Ser Leu Trp Ala Lys Arg Lys
    370                 375                 380

Asn Gly Leu Leu Val Cys Val Phe Glu Lys Thr Pro Cys Asp Tyr Ile
385                 390                 395                 400

Asp Val Met Leu Asn Leu Arg Asp Phe Ser Val Asp Ser Ile Ile Asp
                405                 410                 415

Thr Thr His Phe Leu Glu Asn Phe Asp Lys Lys Lys Gln Gln Glu Ser
            420                 425                 430

Thr Ser Pro Met Thr Glu Lys Lys Thr Val Lys Phe Ala Asn Glu Ile
        435                 440                 445

His Asp Ile Gly Ser Val Ser His Ser Leu Ser Lys Leu Ile Asp Asp
    450                 455                 460

Val Arg Phe Gly Lys Val Phe Ser Ala Asp Asp Leu Leu Pro Leu
465                 470                 475                 480

Ser Ile Arg Val Ala Asn His Val Asn Glu Glu Arg Tyr Phe Thr Leu
                485                 490                 495

Asn Cys Leu Ser Glu Asn Ile Pro Cys Ala Val Thr Thr Ser Val Leu
            500                 505                 510

Glu Asn Glu Ile Lys Leu Lys Ile His Ser Leu Pro Tyr Gln Ala Gly
        515                 520                 525

Leu Phe Ile Val Asp Ser His Thr Leu Ser Leu Leu Ser Phe Asn Lys
    530                 535                 540
```

-continued

```
Ser Val Ala Lys Asn Met Phe Gly Leu Arg Leu His Glu Leu Ala Gly
545                 550                 555                 560

Ser Ser Val Thr Lys Leu Val Pro Ser Leu Ala Asp Met Ile Ser Tyr
                565                 570                 575

Ile Asn Lys Thr Tyr Pro Met Leu Asn Ile Thr Leu Pro Glu Asn Lys
                580                 585                 590

Gly Leu Val Leu Thr Glu His Phe Phe Arg Lys Ile Glu Ala Glu Met
            595                 600                 605

His His Asp Lys Asp Ser Phe Tyr Thr Ser Ile Gly Leu Asp Gly Cys
        610                 615                 620

His Lys Asp Gly Asn Leu Ile Lys Val Asp Val Gln Leu Arg Val Leu
625                 630                 635                 640

Asn Thr Asn Ala Val Leu Leu Trp Ile Thr His Ser Arg Asp Val Val
                645                 650                 655

Ile Glu Asn Tyr Thr Thr Val Pro Ser Gln Leu Pro Met Leu Lys Glu
                660                 665                 670

Asn Glu Ile Asp Val Val Gly Ser Arg Gly Ser Ser Ser Ala Ser Ser
            675                 680                 685

Lys Lys Ser Ser Glu Lys Ile Pro Val Asn Thr Leu Lys Ala Met Ala
690                 695                 700

Asp Leu Ser Ile Ser Ser Ala Glu Thr Ile Ser Asn Ser Asp Asp Glu
705                 710                 715                 720

Val Asp Leu Asn Gln Val Asn Glu Lys Leu Arg Glu Thr Ser Cys Gly
                725                 730                 735

Lys Val Arg Gly Ile Glu Ser Asn Asp Asn Asn Tyr Asp Asp Asp
            740                 745                 750

Met Thr Met Val Asp Asp Pro Glu Leu Lys His Lys Ile Glu Leu Thr
        755                 760                 765

Lys Met Tyr Thr Gln Asp Lys Ser Lys Phe Val Lys Asp Asp Asn Phe
770                 775                 780

Lys Val Asp Glu Lys Phe Ile Met Arg Ile Ile Glu Pro Ile Asn Gly
785                 790                 795                 800

Glu Glu Ile Lys Lys Glu Thr Asn Glu Leu Asp Lys Arg Asn Ser Thr
                805                 810                 815

Leu Lys Ala Thr Tyr Leu Thr Thr Pro Glu Ala Asn Ile Gly Ser Gln
                820                 825                 830

Lys Arg Ile Lys Lys Phe Ser Asp Phe Thr Ile Leu Gln Val Met Gly
            835                 840                 845

Glu Gly Ala Tyr Gly Lys Val Asn Leu Cys Ile His Asn Arg Glu His
850                 855                 860

Tyr Ile Val Ile Lys Met Ile Phe Lys Glu Arg Ile Leu Val Asp
865                 870                 875                 880

Thr Trp Val Arg Asp Arg Lys Leu Gly Thr Ile Pro Ser Glu Ile Gln
                885                 890                 895

Ile Met Ala Thr Leu Asn Lys Asn Ser Gln Glu Asn Ile Leu Lys Leu
            900                 905                 910

Leu Asp Phe Phe Glu Asp Asp Tyr Tyr Tyr Ile Glu Thr Pro Val
        915                 920                 925

His Gly Glu Thr Gly Ser Ile Asp Leu Phe Asp Val Ile Glu Phe Lys
    930                 935                 940

Lys Asp Met Val Glu His Glu Ala Lys Leu Val Phe Lys Gln Val Val
945                 950                 955                 960

Ala Ser Ile Lys His Leu His Asp Gln Gly Ile Val His Arg Asp Ile
```

-continued

```
                965                970                975
Lys Asp Glu Asn Val Ile Val Asp Ser His Gly Phe Val Lys Leu Ile
                    980                985                990
Asp Phe Gly Ser Ala Ala Tyr Ile Lys Ser Gly Pro Phe Asp Val Phe
                    995               1000               1005
Val Gly Thr Met Asp Tyr Ala Ala Pro Glu Val Leu Gly Gly Ser
        1010               1015               1020
Ser Tyr Lys Gly Lys Pro Gln Asp Ile Trp Ala Leu Gly Val Leu
        1025               1030               1035
Leu Tyr Thr Ile Ile Tyr Lys Glu Asn Pro Tyr Tyr Asn Ile Asp
        1040               1045               1050
Glu Ile Leu Glu Gly Glu Leu Arg Phe Asp Lys Ser Glu His Val
        1055               1060               1065
Ser Glu Glu Cys Ile Ser Leu Ile Lys Arg Ile Leu Thr Arg Glu
        1070               1075               1080
Val Asp Lys Arg Pro Thr Ile Asp Glu Ile Tyr Glu Asp Lys Trp
        1085               1090               1095
Leu Lys Ile
        1100

<210> SEQ ID NO 9
<211> LENGTH: 15
<212> TYPE: PRT
<213> ORGANISM: human

<400> SEQUENCE: 9

Ala Met Ala Arg Ala Ala Ser Ala Ala Ala Leu Ala Arg Arg Arg
1               5                   10                  15
```